US007288696B2

(12) United States Patent
Chiang et al.

(10) Patent No.: US 7,288,696 B2
(45) Date of Patent: Oct. 30, 2007

(54) GENETIC ENGINEERING OF SYRINGYL-ENRICHED LIGNIN IN PLANTS

(75) Inventors: Vincent Lee C. Chiang, Cary, NC (US); Laigeng Li, Raleigh, NC (US)

(73) Assignee: Board of Control of Michigan Technological University, Houghton, MI (US)

( * ) Notice: Subject to any disclaimer, the term of this patent is extended or adjusted under 35 U.S.C. 154(b) by 431 days.

(21) Appl. No.: 10/939,794

(22) Filed: Sep. 13, 2004

(65) Prior Publication Data

US 2005/0050585 A1 Mar. 3, 2005

Related U.S. Application Data

(63) Continuation-in-part of application No. 09/947,150, filed on Sep. 5, 2001, now Pat. No. 6,812,377.

(60) Provisional application No. 60/230,086, filed on Sep. 5, 2000.

(51) Int. Cl.
*C12N 15/29* (2006.01)
*C12N 15/82* (2006.01)
*C12N 5/04* (2006.01)
*A01H 5/00* (2006.01)

(52) U.S. Cl. .................. 800/298; 536/23.1; 435/320.1; 435/419; 800/278; 800/287; 800/319

(58) Field of Classification Search ............... 536/23.1; 435/320.1, 419; 800/278, 290, 298, 287
See application file for complete search history.

(56) References Cited

U.S. PATENT DOCUMENTS

| 5,451,514 | A | 9/1995 | Boudet et al. | |
|---|---|---|---|---|
| 5,633,439 | A | 5/1997 | Walter | |
| 5,922,928 | A | 7/1999 | Chiang et al. | |
| 6,066,780 | A | 5/2000 | Boudet et al. | |
| 6,812,377 | B2 * | 11/2004 | Chiang et al. | .............. 800/278 |
| 2002/0062496 | A1 | 5/2002 | Chapple et al. | |
| 2002/0078474 | A1 | 6/2002 | Chiang et al. | |
| 2002/0078477 | A1 | 6/2002 | Chiang et al. | |

FOREIGN PATENT DOCUMENTS

| EP | 1006190 A1 | 12/1998 |
|---|---|---|
| WO | WO 99/31243 | 6/1999 |
| WO | WO 00/46382 | 8/2000 |
| WO | WO 01/27241 A2 | 4/2001 |

OTHER PUBLICATIONS

Hu et al (1999, Nature Biotechnology 17:808-812).*
Kajita et al (1997, Plant Science 128:109-118).*
Piquemal et al (1998, Plant Journal 13(1) :71-83).*
Franke et al (2000, Plant Journal 22(3):223-234).*
Bowie et al, Science 247:1306-1310, 1990.*
McConnell et al, Nature 411 (6838):709-713, 2001.*

Baucher, Marie, et al., "Red xylem and higher lignin extractability by down-regulating a cinnamyl alcohol dehydrogenase in poplar," *Plant Physiol.* 112:1479 (1996).
Bevan, Michael et al., "A chimaeric antibiotic resistance gene as a selectable marker for plant cell transformation," *Nature*, 304:184 (Jul. 14, 1983).
Bland, David E., "Colorimetric and chemical identification of lignins in different parts of Eucalyptus Botryoides and their relation to lignification," *Holzforschung*, 20:12 (1966).
Boudet, A. M., et al., "Tansley review No. 80: Biochemistry and molecular biology of lignification," *New Phytol.* 129:203 (1995).
Bowie, et al., *Science*, 247:1306-10 (1990).
Brill, Elizabeth M., et al., "Molecular characterisation and expression of a wound-inducible cDNA encoding a novel cinnamyl-alcohol dehydrogenase enzyme in lucerne (*Medicago sativa* L.)," *Plant. Mol. Biol.* 41:279 (1999).
Bugos, Robert C., "cDNA cloning, sequence analysis and season expression of lignin-bispecific caffeic acid/5-hydroxyferulic acid O-methyltransferase of aspen," *Plant Mol. Biol.*, 17:1203 (1991).
Chandler, Vicki L., et al., "Two regulatory genes of the maize anthocyanin pathway are homologous: Isolation of *B* utilizing *R* genomic sequences," *The Plant Cell*, 1:1175 (1989).
Chang, Hou-min, and Sarkanen, K.V., "Species variation in lignin: Effect of species on the rate of Kraft delignification," *Tappi 56*: 132 (1973).
Chen, Fang, et al., "Evidence for a novel biosynthetic pathway that regulates the ratio of syringyl to guaiacyl residues in lignin in the differentiating xylem of *Magnolia kobus* DC,"*Planta* 207:597 (1999).
Chiang, Vincent L. and Funaoka, Masamitsu, "The difference between guaiacyl and guaiacyl-syringyl lignins in their responses to Kraft delignification," *Holzforschung* 44:309 (1990).
Corner, E.J.H., *"The Life of Plants,"* New American Library, NY, NY. (1968).
Ebert, Paul R., et al., "Identification of an essential upstream element in the nopaline synthase promoter by stable and transient assays," *PNAS USA*, 84:5745 (1987).
Ellis, D.D., et al., "Stable transformation of *Picea glauca* by particle acceleration," *Bio/Technology* 11:84 (1993).
Esau, Katherine, *"Anatomy of Seed Plants,"* 2d ed., John Wiley & Sons, NY., NY (1965).
Fergus, B.J., and Goring, D.A.I., "The location of guaiacyl and syringyl lignins in birch xylem tissue," *Holzforschung* 24:113 (1970a).
Fergus, B.J., and Goring, D.A.I., "The distribution of lignin in birch wood as determined by ultraviolet microscopy," *Holzforschung* 24:118 (1970b).
Fourgoux-Nicol, et al., *Plant Molecular Biology*, 40:857-872 (1999).

(Continued)

*Primary Examiner*—Stuart F. Baum
(74) *Attorney, Agent, or Firm*—Michael Best & Friedich LLP

(57) ABSTRACT

The present invention relates to a novel DNA sequence, which encodes a previously unidentified lignin biosynthetic pathway enzyme, sinapyl alcohol dehydrogenase (SAD) that regulates the biosynthesis of syringyl lignin in plants. Also provided are methods for incorporating this novel SAD gene sequence or substantially similar sequences into a plant genome for genetic engineering of syringyl-enriched lignin in plants.

15 Claims, 10 Drawing Sheets

OTHER PUBLICATIONS

Frankie, et al., *Plant Journal*, 22(3):223-224 (2000).

Freudenberg, Karl, "Lignin: Its constitution and formation from p-hydroxycinnamyl alcohols," *Science* 148:595 (1965).

Frey-Wyssling, A., and Bosshard, H.H., "Cytology of the ray cells in sapwood and heartwood," *Holzforschung* 13:129-137 (1959).

Galliano, Helene, et al., Molecular cloning, sequence analysis and elicitor-/ozone-induced accumulation of cinnamyl alcohol dehydrogenase from Norway spruce (*Picea abies L.*), *Plant Mol. Biol*, 23:145 (1993a).

Galliano, Helene, et al., "Ozone induction and purification of spruce cinnamyl alcohol dehydrogenase," *Phytochemistry* 32:557 (1993b).

Goffner, D., et al., "Purification and characterization of isoforms of cinnamyl alcohol dehydrogenase from *Eucalyptus xylem*," *Planta* 188:48 (1992).

Goffner, Deborah, et al., "Purification and characterization of cinnamoyl-coenzyme A:NADP oxidoreductase in *Eucalyptus gunnii*," *Plant Physiol.* 106:625 (1994).

Goffner, Deborah, et al., "A novel aromatic alcohol dehydrogenase in higher plants: molecular cloning and expression," *Plant Mol. Biol.* 36:755-765 (1998).

Grand, Claude, et al., "Natural variations and controlled changes in lignification process," *Holzforschung* 36:217-223 (1982).

Grima-Pattenati, J, et al., "Molecular cloning and expression of a *Eucalyptus gunnii* cDNA clone encoding cinnamyl alcohol dehydrogenase," *Plant Mol. Biol.* 21:1085-1095 (1993).

Grima-Pettanati, Jacqueline, et al., "Purification and characterization of cinnamyl alcohol dehydrogenase isoforms from *Phaseolus Vulgaris*," *Phytochemistry* 37:941-947 (1994).

Gross, G.G., *Advances in Botanical Research*, ed. By H.W. Woolhouse, 8:25, Academic Press, London (1980).

Guo, Dianjing, et al., "Downregulation of caffeic acid 3-0-methyltransferase and caffeoyl CoA 3-0-methyltransferase in transgenic alfalfa: impacts on lignin structure and implications for the biosynthesis of G and S lignin," *Plant Cell*, 13: 73-88 (Jan. 2001).

Hahlbrock, Klaus, and Schell, Dierk, "Physiology and molecular biology of phenylpropanoid metabolism," *Plant Mol. Biol.* 40:347-369 (1989).

Halpin, Claire, et al., ", "Purification and characterization of cinnamyl alcohol dehydrogenase from tobacco stems, *Plant Physiol.*, 98:12-16 (1992).

Halpin, Claire, et al., "Manipulation of lignin quality by downregulation of cinnamyl alcohol dehydrogenase," *Plant Physiol.*, 98:12-16 (1992).

Hawkins, Simon William, and Boudet, Alain Michael, "Purification and characterization of cinnamyl alcohol dehydrogenase isoforms from the periderm of *Eucalyptus gunnii* Hook," *Plant Physiol.*, 104:75-84 (1994).

Hibino, Takashi, et al., "Purification and partial sequences of *Aralia cordata* cinnamyl alcohol dehydrogenase," *Phytochemistry*, 32:565-567 (1993)a).

Hibino, Takashi, et al., "Cinnamyl alcohol dehydrogenase from *Aralia cordata*: Cloning of the cDNA and expression of the gene in lignified tissues," *Plant Cell Physiol.*, 34:659-665 (1993).

Higuchi, T., "Biochemistry and Molecular Biology of Wood,", *Springer Series in Wood Science*, ed. T.E. Timell, Springer-Verlag, NY, NY (1997).

Higuchi, Takayoshi, et al., "Red-brown color of lignified tissues of transgenic plants with antisense CAD gene: wine-red lignin from coniferyl aldehyde," *J. Biotechnol.*, 37:151-158 (1994).

Hill, et al., *Biochem. Biophys. Res. Comm.*, 244:573-577 (1998).

Hu, Wen-jing, et al., "Compartmentalized expression of two structurally and functionally distinct 4-coumarate: CoA ligase genes in aspen (*Populus tremuloides*)," *Proc. Natl. Acad. Sci* USA, 95:5407-5412 (Apr. 1998).

Hu, Wen-Jing, et al., "*Repression of lignin biosynthesis promotes cellulose accumulation and growth in transgenic trees*,"*Nat. Biotechnol.*, 17:808 (1999).

Hudspeth, Richard L., and Grula, John W., "Structure and expression of the maize gene encoding the phosphoenolypruvate carboxylase isozyme involved in $C_4$ photosynthesis," *Plant Mol. Biol.*, 12:579-589 (1989).

Humphreys, John M., et al., "New routes for lignin biosynthesis defined by biochemical characterization of recombinant ferulate 5-hydroxylase, a multifunctional cytochrome P450-dependent monooxygenase," *Proc. Natl. Acad. Sci. USA*, 96:10045-10050 (Aug. 1999).

Jefferson, et al., *Plant Molecular Biology Reporter*, 5:387 (1987).

Jornvall, et al., "Characteristics of alcohol/polyol dehydrogenase the zinc-containing long-chain alcohol dehydrogenases," *Eur. J. Biochem.*, 167:195-201 (1987).

Kajita et al., *Plant Science*, 128:109-118 (1997.

Kawamura, Ichiji, et al., "Studies on the lignin of young tissues of wood," *J. Jpn. Wood Res. Soc.*, 8:148-153 (1962), In Japanese only.

Knight, M.E., et al., "Identification and characterisation of cDNA clones encoding cinnamyl alcohol dehydrogenase from tobacco," *Plant Mol. Biol.* 19:793-801 (1992).

Kutsuki, Hidetoshi, et al., "Regulatory role of cinnamyl alcohol dehydrogenase in the formation of guaiacyl and syringyl lignins," *Phytochemistry*, 21(1):19-23 (1982).

Lacombe, Eric, et al., "Cinnamoyl CoA reductase, the first committed enzyme of the lignin branch biosynthetic pathway: cloning, expression and phylogenetic relationships," *Plant J.*, 11(3):429-441 (1997).

Lawton, Michael A., et al., "Expression of a soybean β-conclycinin gene under the control of the Cauliflower Mosaic Virus 35S and 19S promoters in transformed petunia tissues," *Plant Mol. Biol.*, 9:315-324 (1997).

Lazar, et al., *Molecular and Cellular Biol.*, 8:1247-1252 (1988).

Leyva, Antonio, et al., "Cis-element combinations determine phenylalanine ammonia-lyase gene tissue-specific expression patterns," *The Plant Cell*, 4:263-271 (Mar. 1992).

Li, Laigeng, et al., "A novel multifunctional O-methyltransferase implicated in a dual methylation pathway associated with lignin biosynthesis in loblolly pine," *Proc. Natl. Acad. Sci. USA*, 94:5461-5466 (1997).

Li, Laigeng, et al., "Secondary xylen-specific expression of caffeoyl-coenzyme A 3-O-methyltransferase plays an important role in the methylation pathway associated with lignin biosynthesis in loblolly pine," *Plant Mol. Biol.*, 40:555-565 (1999).

Li, Laigene, et al., "5-hydroxyconiferyl aldehyde modulates enzymatic methylation for syringyl monolignol formation, a new view of monolignol biosynthesis in angiosperms," *J. Biol. Chem.*, 275(9): 6537-6545 (2000).

Li, Laigeng, et al., "The last step of syringyl monolignol biosynthesis in angiosperms is regulated by a novel gene encoding sinapyl alcohol dehydrogenase," *The Plant Cell*, 13:1567-1585 (2001).

Lüderitz, Thomas, and Grisebach, Hans, "Enzymic synthesis of lignin precursors comparion of cinnamoyl-CoA reductase and cinnamyl alcohol: NADP + dehydrogenase from spruce (*Picea abies L.*) and soybean (*Glycine max L.*)," *Eur. J. Biochem.*, 119:115-124 (1981).

Mackay, John J., et al., "Genetic analysis of cinnamyl alcohol dehydrogenase in loblolly pine: single gene inheritance, molecular characterization and evolution," *Mol. Gen. Genet.*, 247:537-545 (1995).

Mansell, Richard L., et al., "Purification and properties of cinnamyl alcohol dehydrogenase from higher plants involved in lignin biosynthesis," *Phytochemistry*, 13: 2427-2435 (1974).

Mansell, Richard L., et al., "Multiple forms and specificity of coniferyl alcohol dehydrogenase from cambial regions of higher plants," *Phytochemistry*, 15: 1849-1853 (1976).

McConnell, et al., *Nature*, 411 (6868):709-713 (2001).

Medina-Escobar et al., NCBI Accession No. U63534 (Jan. 29, 1999).

Musha, Y., and Gorin, D.A.I., "Distribution of syringyl and guaiacyl moieties in hardwoods as indicated by ultraviolet microscopy," *Wood Sci. Technol.*, 9:45-58 (1975).

Nakano, J., and Meshitsuka, G., *Methods in lignin chemistry*, S. W. Lin, and C.W. Dence, eds., Springer-Verlag, NY, NY. 23 (1992).

Napoli, Carolyn, et al., "Introduction of a chimeric chalcone synthase gene into petunia results in reversible co-suppression of homologous genes in trans," *The Plant Cell*, 2:279-289 (Apr. 1990).

Needleman, Saul B., and Wunsch, Christian D., "A general method applicable to the search for similarities in the amino acid sequence of two proteins," *J. Mol. Biol.* 48:448-453 (1970).

Odell, Joan T., et al., "Identifications of DNA sequences required for activity of the cauliflower mosaic virus 35S promoter," *Nature*, 313:810 (1985).

O'Malley, David M., et al., "Purification, characterization, and cloning of cinnamyl alcohol dehydrogenase in loblolly pine (*Pinus taeda* L. )," *Plant Physiol.*, 98:1364-1371 (1992).

Osakabe, Keishi, et al., "Coniferyl aldehyde 5-hydroxylation and methylation direct syringyl lignin biosynthesis in angiosperms," *Proc. Nat. Acad. Sci. USA*, 96(16):8955-8960 (Aug. 1999).

Parvathi, Kota, et al., "Substrate preferences of O-methyltransferases in alfalfa suggest new pathways for 3-O-methylation of monolignols," *Plant J.*, 25(2):193-202 (2001).

Piquemal, Joel, et al., "Down-regulation of cinnamoyl-CoA reductase induces significant changes of lignin profiles in transgenic tobacco plants," *The Plant J.*, 13(1):71-83 (1998).

Raven, et al., *Advances in Botanical Research*, H.W. Woolhouse, ed., Academic Press, London, p. 153 (1977).

Rolando, et al., *Methods in Lignin Chemistry*, S. Y. Lin and C.W. Dence, Eds., Springer-Verlag, NY., NY., p. 334 (1992).

Ryser, Ulrich, and Keller, Beat, "Ultrastructural localization of a bean glycine-rich protein in unlignified primary walls of protoxylem cells," *Plant Cell*, 4:773-783 (1992).

Saka, S., and Goring, D.A.I., "The distribution of lignin in white birch wood as determined by bromination with TEM-EDXA," *Holzforschung*, 42(3): 149-153 (1988).

Saka, S., and Goring, D.A.I., *Biosynthesis and biodegradation of wood components*, T. Higuchi, ed., p. 141, Academic Press, NY, NY. (1985).

Samaj, Jozef, et al., "Immunolocalization of cinnamyl alcohol dehydrogenase 2 (CAD 2) indicates a good correlation with cell-specific activity of CAD 2 promoter in transgenic poplar shoots," *Plants*, 204:437-443 (1998).

Sambrook, et al., "*Molecular Cloning: A Laboratory Manual*," Cold Spring Harbor Laboratory, New York, NY (1982).

Sarkanen, et al., "*Lignins occurrence, formation, structure and reactions*,", K.V. Sarkanen and C.H. Ludwig, eds., p. 43, Wiley-Interscience, NY, NY (1971).

Sarkanen, and Ludwig, C.H., eds. (New York: Wiley-Interscience), 19.

Sarni, Farid, et al., "Purification and properties of cinnamoyl-CoA reductase and cinnamyl alcohol dehydrogenase from poplar stems (*Populus X euramericana*)," *Eur. J. Biochem.*, 139:259-265 (1984).

Sato, Yasushi, et al., "Changes in the activity and mRNA of cinnamyl alcohol dehydrogenase during tracheary element differentiation in zinnia," *Plant Physiol.*, 113:425-430 (1997).

Scurfield, G., Reaction wood: its structure and function, *Science*, 179:647 (1973).

Scurfield, G., et al., "The anatomy and chemistry of "rubbery" wood in apple var. lord lambourne," *J. Hort. Sci.*, 38:297-306 (1963).

Somssich, Imre E., et al., "Differential early activation of defense-related genes in elicitor-related parsley cells," *Plant Mol. Biol*, 12:227-234 (1989).

Somssich, Imre E., et al., "*Arabidopsis thaliana* defense-related protein ELI3 is an aromatic alcohol: NADP+ oxidoreductase," *Proc. Natl. Acad. Sci USA*, 93:14199-14203 (1996).

Stewart, Derek, et al., "Fourier-transform infrared and Raman spectroscopic evidence for the incorporation of cinnamaldehydes into the lignin of transgenic tobacco (*Nicotiana tabacum* L. ) plants with reduced expression of cinnamyl alcohol dehydrogenase," *Planta*, 201:311-318 (1997).

Sullivan, Thomas D., "Isolation and characterization of a maize chlorophyll a/b binding protein gene that produces high levels of mRNA in the dark," *Mol. Gen. Genet.*, 215:431-440 (1989).

Terashima, Noritsugu, et al., "Heterogeneity in formation of lignin," *Holzforschung*, 42:101-105 (1986).

Towers, G.H.N., and Gibbs, R.D., "Lignin chemistry and the taxonomy of higher plants," *Nature*, 172:25 (1953).

Trotter, Patrick C., "Biotechnology in the pulp and paper industry: a review," *Tech. Assoc. Pulp Paper Ind.* J., 73:198 (1990).

Tsai, Chung-Jui, et al., "Suppression of O-methyltransferase gene by homologous sense transgene in quaking aspen causes red-brown wood phenotypes," *Plant Physiol.*, 117:101-112 (1998).

Tsai, Chung-Jui, et al., "*Agrobacterium*-mediated transformation of quaking aspen (*Populus tremuloides*) and regeneration of transgenic plants," *Plant Cell Reports*, 14:94-97 (1994).

Umezawa, T., "Lignans," *Biochemistry and Molecular Biology of Wood*, Sec. 4.3.5:181-194 (QK 647.H53 1997), English trans.

Umezawa, T., *Wood Molecular Biology*, T. Higuchi, Ed. (Tokyo: Buneido Publishing), 140 (1994).

Van Der Krol, Alexander R., et al., "An anti-sense chalcone synthase gene in transgenic plants inhibits flower pigmentation," *Nature*, 333:866-869 (1988).

Van Doorsselaere, Jan, et al., "Isolation of cinnamyl alcohol dehydrogenase cDNAs from two important economic species: alfalfa and poplar. Demonstration of a high homology of the gene within angiosperms," *Plant Physiol. Biochem.*, 33:105-109 (1995).

Wang, Yixin, et al., "Characterization of *cis*-acting elements regulating transcription from the promoter of a constitutively active rice actin gene," *Mol. Cell. Biol.*, 12:3399-3406 (Aug. 1992).

Walker, John C., et al., "DNA sequences required for anaerobic expression of the maize alcohol dehydrogenase 1 gene," *PNAS USA*, 84:6624-6628 (Oct. 1997).

Wardrop, A.B., "*Lignins: occurrence, formation, structure and reactions*," K.V. Sarkanen and C.H. Ludwig, eds., Wiley-Interscience, NY, NY; 19 (1971).

Wardrop, A.B., "*Xylem cell development*," J.R. Barnett, Ed., *Castle House Publications*, Tunbridge Wells, UK; 115 (1981).

Wardrop, A.B., and Dadswell, H.E., "The cell wall structure of xylem parenchyma," *Aust. J. Sci. Res. Ser. B Biol. Sci*, 5:223 (1952).

Wardrop, A.B., and Davies, G.W., "The nature of reaction wood," *Aust. J. Bot.*, 12:24-38 (1964).

Wengenmayer, Jurgen, et al., "Enzymic synthesis of lignin precursors," *Eur. J. Biochem.*, 65:529-536 (1976).

Whetten, R., et al., "Lignin biosynthesis," *Plant Cell*, 7:1001-1013 (Jul. 1995).

Whetten, Ross W., et al., "Recent advances in understanding lignin biosynthesis," *Annu. Rev. Plant Physiol. Plant Mol. Biol.*, 49:585-609 (1998).

Wittich, P.E., et al., "Immunolocalization of the petunia floral binding proteins 7 and 11 during seed development in wild-type and expression mutants, of *Petunia hybrida*," *Protoplasma*, 208:224-229 (1999).

Wu, Luguang, et al., "A xylem-specific cellulose synthase gene from aspen (*Populus tremuloides*) is responsive to mechanical stress," *Plant J.*, 22(6):495-502 (2000).

Wyrambik, Dorothea, and Grisebach, Hans, "Purification and properties of isoenzymes of cinnamyl-alcohol dehydrogenase from soybean-cell-suspension cultures," *Eur. J. Biochem.*, 59:9-15 (1975).

Wyrambik, Dorothea, and Grisebach, Hans, "Enzymic synthesis of lignin precursors," *Eur. J. Biochem.*, 97:503-509 (1979).

Yang, N.S., and Russell, D., "Maize sucrose synthase-1 promoter directs phloem cell-specific expression of *Gus* gene in transgenic tobacco plants," *PNAS USA*, 87:4144-4148 (Jun. 1990).

Ye, Zheng-Hua, et al., "An alternative methylation pathway in lignin biosynthesis in zinnia," *The Plant Cell*, 6:1427-1439 (Oct. 1994).

Zhang, Xing-Hai, and Chiang, Vincent L., "Molecular cloning of 4-coumerate: coenzyme A ligase in loblolly pine and the roles of this enzyme in the biosynthesis of lignin in compression wood," *Plant Physiol.* 113:65-74 (1997).

Zhong, Ruigin, et. al., "Dual mathylation pathways in lignin biosynthesis," *Plant Cell*, 10:2033:-2045 (Dec. 1998).

Zinser, Christian, et al., "Induction of stilbene synthase and cinnamyl alcohol dehydrogenase mRNAs in scots pine (*Pinus sylvestris* L.) seedlings," *Planta*, 204:169-176 (1998).

Li, et al., GENBANK, Accession No. AF273256, Plant Cell 13(7): 1567-1586 (2001).

Li, and Chiang, GENBANK Accession No. 217957, Plant Biotechnology Research Cent4er, School of Forestry and Wood Products, Mich. Tech. Univ. 1400 Townsend Dr., Houghton, MI 49931 USA, Submitted Dec. 20, 1999.

Melis et al., GENBANK Accession No. AF038561, *Plant Physiol* 116:1191 (1998).

Knight, et al., GENBANK Accession No. X62343, *Plant Mol. Biol.* 19(5):793-801 (1992).

Brill et al. GENBANK Accession No. AF083332, *Plant Mol. Biol.* 41(2):279-291 (1999).

Kim, S-J. et al., "Functional reclassification of the putative cinnamyl alcohol dehydrogenase multigene family in Arabidopsis," Proc. Natl. Aca. Sci. USA (2004) 101(6):1455-1460.

Li, L. et al., "The last step of syringyl monolignol biosynthesis in angiosperms is regulated by a novel gene encoding sinapyl alcohol dehydrogenase," The Plant Cell (2001) 13:1567-1585.

Mitchell, H.J. et al., "Differential induction of cinnamyl alcohol dehydrogenase during defensive lignification in wheat (*Triticum aestivum* L.): characterisation of the major inducible form," Planta (1999) 208:31-37.

\* cited by examiner

Schematic Representation of Plant Monolignol Pathways for Production of Coniferyl Alcohol and Sinapyl Alcohol

FIG. 2A
SAD cDNA Sequence

```
TTTTTTTTTT TTTCCTAGCC TTCCTTCTCG ACGATATTTC TCTATCTGAA
GCAAGCACCA TGTCCAAGTC ACCAGAAGAA GAACACCCTG TGAAGGCCTT
CGGGTGGGCT GCTAGGGATC AATCTGGTCA TCTTTCTCCC TTCAACTTCT
CCAGGAGGGC AACTGGTGAA GAGGATGTGA GGTTCAAGGT GCTGTACTGC
GGGATATGCC ATTCTGACCT TCACAGTATC AAGAATGACT GGGGCTTCTC
CATGTACCCT TTGGTTCCTG GCATGAAAT TGTGGGGAA GTGACAGAAG
TTGGGAGCAA GGTGAAAAAG GTTAATGTGG GAGACAAAGT GGGCGTGGGA
TGCTTGGTTG GTGCATGTCA CTCCTGTGAG AGTTGTGCCA ATGATCTTGA
AAATTACTGT CCAAAAATGA TCCTGACATA CGCCTCCATC TACCATGACG
GAACCATCAC TTACGGTGGC TACTCAGATC ACATGGTCGC TAACGAACGC
TACATCATTC GATTCCCCGA TAACATGCCG CTTGACGGTG GCGCTCCTCT
CCTTTGTGCC GGGATTACAG TGTATAGTCC CTTGAAATAT TTTGGACTAG
ATGAACCCGG TAAGCATATC GGTATCGTTG GCTTAGGTGG ACTTGGTCAC
GTGGCTGTCA AATTTGCCAA GGCCTTTGGA TCTAAAGTGA CAGTAATTAG
TACCTCCCCT TCCAAGAAGG AGGAGGCTTT GAAGAACTTC GGTGCAGACT
CATTTTTGGT TAGTCGTGAC CAAGAGCAAA TGCAGGCTGC CGCAGGAACA
TTAGATGGCA TCATCGATAC AGTTTCTGCA GTTCACCCCC TTTTGCCATT
GTTTGGACTG TTGAAGTCTC ACGGGAAGCT TATCTTGGTG GGTGCACCGG
AAAAGCCTCT TGAGCTACCT GCCTTTTCTT TGATTGCTGG AAGGAAGATA
GTTGCCGGGA GTGGTATTGG AGGCATGAAG GAGACACAAG AGATGATTGA
TTTTGCAGCA AAACACAACA TCACAGCAGA TATCGAAGTT ATTTCAACGG
ACTATCTTAA TACGGCGATA GAACGTTTGG CTAAAAACGA TGTCAGATAC
CGATTCGTCA TTGACGTTGG CAATACTTTG GCAGCTACGA AGCCCTAAGG
AGAAGATCCC ATGTTCTCGA ACCCTTTATA AAATCTGATA ACATGTGTTG
ATTTCATGAA TAAATAGATT ATCTTTGGGA TTTTTCTTTA ATAAACGAAG
TGTTCTCGAA AACTTAACAT CGGCAATACC CTGGCAGCTA CGAGAAACGC
TTTAGAATTG TTTGTAAGTT TGTTTCATTA GGGTGATACC ATGCTCTCGA
GTCCTTTGTA AGATCCATTT ATAGTTGCGT GAATGCTATG AACAAATAAT
ATGTTTGCGG CTTCTCTTCA AAAAAAAAAA AAAAAAAAA AAAAAA
```

FIG. 2B
SAD Protein Sequence

MSKSPEEEHP VKAFGWAARD QSGHLSPFNF SRRATGEEDV RFKVLYCGIC
HSDLHSIKND WGFSMYPLVP GHEIVGEVTE VGSKVKKVNV GDKVGVGCLV
GACHSCESCA NDLENYCPKM ILTYASIYHD GTITYGGYSD HMVANERYII
RFPDNMPLDG GAPLLCAGIT VYSPLKYFGL DEPGKHIGIV GLGGLGHVAV
KFAKAFGSKV TVISTSPSKK EEALKNFGAD SFLVSRDQEQ MQAAAGTLDG
IIDTVSAVHP LLPLFGLLKS HGKLILVGAP EKPLELPAFS LIAGRKIVAG
SGIGGMKETQ EMIDFAAKHN ITADIEVIST DYLNTAIERL AKNDVRYRFV
IDVGNTLAAT KP

Phylogenetic Analysis of Aspen SAD and Plant CADs

Molecular Characterization of Aspen PtCAD and PtSAD

HPLC-UV/MS Analysis of Recombinant PtCAD and PtSAD Reactions

Inhibition Kinetics of PtCAD and PtSAD

Detection of Guaiacyl and Syringyl Lignins in Aspen Stem

Immunolocalization of PtCAD, PtCAld5H, and PtSAD Proteins in Aspen Stem

Immunoblot Detection of CAD and SAD Proteins in Various Plants

GENETIC ENGINEERING OF SYRINGYL-ENRICHED LIGNIN IN PLANTS

CROSS-REFERENCE TO RELATED APPLICATIONS

This application is a continuation in part of U.S. application Ser. No. 09/947,150, filed Sep. 5, 2001, now U.S. Pat. No. 6,812,377, and claims the benefit of U.S. Provisional Application No. 60/230,086, filed on Sep. 5, 2000, each of which is incorporated by reference herein.

BACKGROUND OF THE INVENTION

The invention relates to a novel DNA sequence, which encodes a previously unidentified lignin biosynthetic pathway enzyme, sinapyl alcohol dehydrogenase (SAD), that regulates the biosynthesis of syringyl lignin in plants. Methods for incorporating this novel SAD gene sequence or sequences similar to this SAD gene into plant genome for genetic engineering of syringyl-enriched lignin in plants are also provided.

Lignin, a complex phenolic polymer, is a major part of the supportive structure of most woody plants including angiosperm and gymnosperm trees which, in turn, are the principal sources of fiber for making paper and cellulosic products. Lignin generally constitutes about 25% of the dry weight of the wood, making it the second most abundant organic compound on earth after cellulose. Lignin provides rigidity to wood for which it is well suited due, in part, to its resistance to biochemical degradation.

Despite its importance to plant growth and structure, lignin is nonetheless problematic to post-harvest, cellulose-based wood/crop processing for fiber, chemical, and energy production because it must be removed or degraded from cellulose at great expense. Certain structural constituents of lignin, such as the guaiacyl moiety, promote monomer cross-linkages that increase lignin resistance to degradation (Sarkanen, 1971; Chang and Sarkanen, 1973; Chiang and Funaoka, 1990). In angiosperms, lignin is composed of a mixture of guaiacyl and syringyl monolignols, and can be degraded at considerably less energy and chemical cost than gymnosperm lignin, which consists almost entirely of guaiacyl moieties (Freudenberg, 1965). It has been estimated that, if syringyl lignin through genetic engineering, could be incorporated into gymnosperm guaiacyl lignin or into angiosperms to increase the syringyl lignin content, the annual saving in processing of such genetically engineered plants as opposed to their wild types would be in the range of $6 to $10 billion in the U.S. alone. Consequently, there has been long-standing incentive to understand the biosynthesis of syringyl monolignol to genetically engineer plants to contain more syringyl lignin, thus, facilitating wood/crop processing (Trotter, 1990; Bugos et al., 1991; Boudet et al., 1995; Hu et al., 1999).

Although it has been known that syringyl lignin is derived from guaiacyl lignin, only a partial syringyl monolignol pathway and its genes encoding the enzymes that catalyze the steps of the pathway have been uncovered. This partial syringyl monolignol pathway, which diverges from guaiacyl pathway at coniferaldehyde, is mediated by genes encoding the enzymes coniferyl aldehyde 5-hydroxylase (CAld5H) (Osakabe et al., 1999) and S-adenosyl-L-methionine (SAM)-dependent 5-hydroxyconiferaldehyde O-methyl-transferase (AldOMT) (Li et al., 2000), respectively, for the formation of sinapaldehyde (see, FIG. 1). However, sinapaldehyde must be enzymatically converted into sinapyl alcohol, the syringyl monolignol, for the biosynthesis of syringyl lignin in plants (see, FIG. 1). The gene encoding such an enzyme, i.e., a sinapyl alcohol dehydrogenase (SAD), has never been identified nor cloned and represents a missing gene that is indispensable for genetic engineering of syringyl lignin in plants. Thus, there is a need for the identification and isolation of this key gene (SAD) for genetic augmentation of syringyl monolignol biosynthesis in plants and for the methods for such genetic manipulation comprising the use of this key gene.

BRIEF SUMMARY OF THE INVENTION

The present invention provides an isolated complete DNA sequence encoding a novel enzyme, sinapyl alcohol dehydrogenase, SAD, that is obligatory to and plays a dominant role in the biosynthesis of syringyl lignin in plants. SAD catalyzes the conversion of sinapaldehyde to sinapyl alcohol, the syringyl monolignol. The production of SAD, and hence, the production of syringyl monolignol may be increased by supplying extra copies of the SAD gene, or decreased by insertion of the SAD gene or a portion thereof into the genome of a plant, in antisense orientation so that the amount of SAD for catalyzing the sinapyl alcohol is reduced, if so desired.

In one aspect, the invention provides whole gymnosperm plants containing genes which increase production of syringyl lignin and repress production of guaiacyl lignin. Thus the invention addresses the problem of providing gymnosperm species which are easier to delignify in pulping processes.

In another aspect, the invention provides a method for making an expression cassette insertable into a gymnosperm cell for the purpose of inducing formation of syringyl lignin in a gymnosperm plant derived from the cell.

In an additional aspect, the present invention provides a method for modifying genes involved in lignin biosynthesis in gymnosperm species so that production of syringyl lignin is increased while production of guaiacyl lignin is suppressed.

The invention advantageously identifies, isolates, and/or clones those genes in angiosperms responsible for production of syringyl lignin. The invention also advantageously provides for identification and isolation of a polynucleotide encoding a sinapyl alcohol dehydrogenase (SAD) from an angiosperm species and for the use of such polynucleotide to alter the lignin biosynthesis in a gymnosperm.

BRIEF DESCRIPTION OF THE DRAWINGS

FIG. 2 illustrates a SAD polynucleotide DNA sequence (SEQ ID NO: 1) and its corresponding SAD amino acid sequence (SEQ ID NO: 2), FIGS. 2A and 2B respectively;

DETAILED DESCRIPTION OF THE INVENTION

Figure 1:
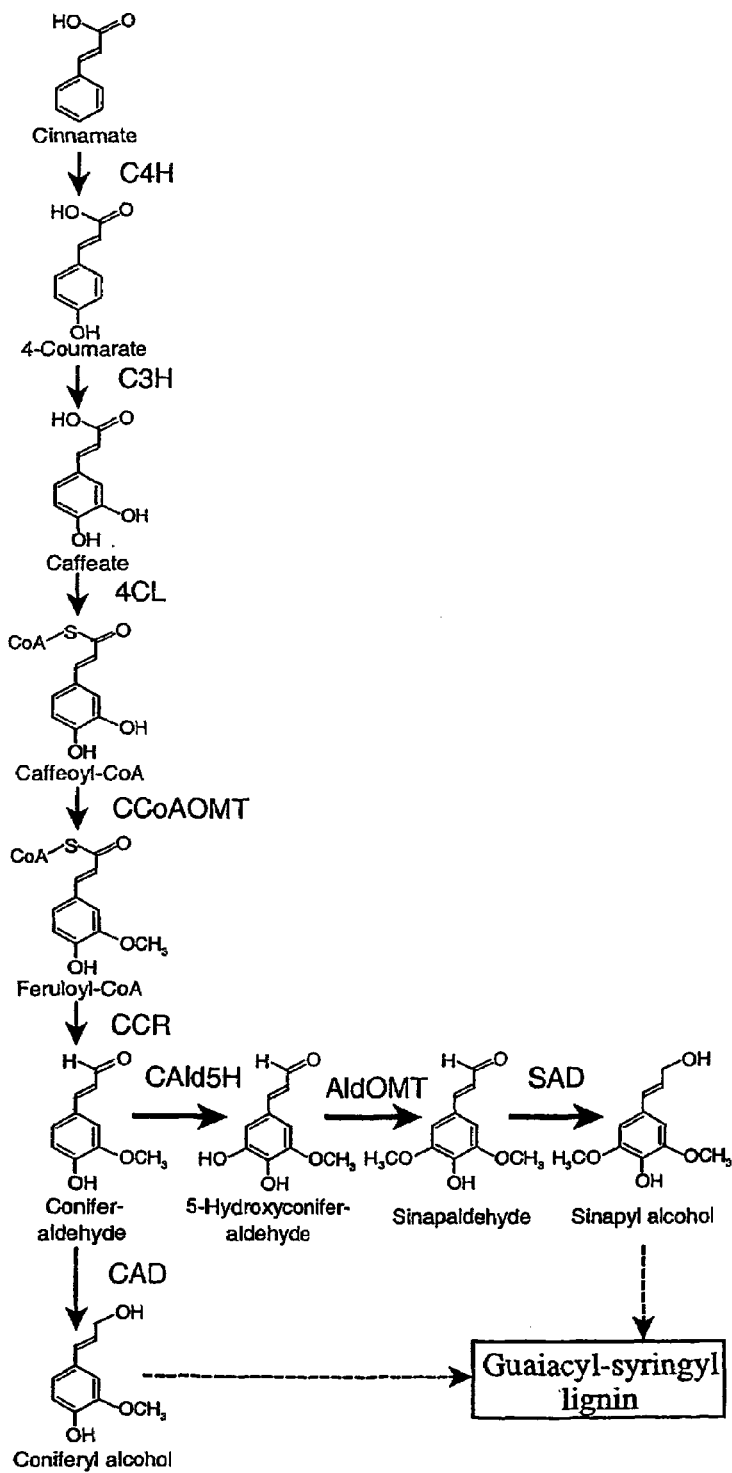
FIG. 1 is a schematic representation of plant monolignol pathways for production of coniferyl alcohol and sinapyl alcohol.

The present invention relates to a polynucleotide sequence encoding sinapyl alcohol dehydrogenase (SAD), the last key enzyme in syringyl monolignol biosynthesis and provides an isolated DNA sequence encoding SAD. The invention further provides a method of altering the lignin composition, i.e., producing syringyl-enriched lignin in transformed plants comprising the sequence. Expression of the SAD coding sequence in transformed plants are expected to exhibit increased syringyl content of the lignin polymer.

The present invention is of particular value to the paper and pulp industries because lignin containing higher syringyl monomer content is more susceptible to chemical delignification. Currently, vast amounts of energy and time are consumed in the delignification process. Woody plants transformed with an active SAD gene offer a significant advantage in the delignification process over conventional paper feedstocks. Similarly, modification of the lignin composition in grasses by the insertion and expression of a heterologous SAD gene offers a unique method for increasing the digestibility of grasses and is of significant potential economic benefit to the farm and agricultural industries.

The invention provides a SAD coding sequence and a DNA construct useful for the transformation of plant tissue to alter the lignin monomer composition. Plants suitable for transformation in accordance with the present invention include plants that naturally lack syringyl lignin or those that accumulate lignin with a high guaiacyl-syringyl ratio. Plants also suitable for transformation in accordance with the present invention include plants whose lignin could be modified using antisense transformation constructs that reduce the syringyl contents of the transgenic plants' lignin if such an alteration is desirable. Specifically, suitable plants include, but are not limited to gymnosperms, angiosperms, grasses, legumes, forage crops and the like.

The terms used in this specification generally have their ordinary meanings in the art, within the context of the invention and in the specific context where each term is used. Certain terms are discussed below, or elsewhere in the specification, to provide additional guidance to the person of skill in the art in describing the compositions and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

As used herein, "gene" refers to a nucleic acid fragment that expresses a specific protein including the regulatory sequences preceding (5' noncoding) and following (3' noncoding) the coding region. "Native" gene refers to the gene as found in nature with its own regulatory sequences.

"Non-coding region" refers to that portion of the gene that does not directly encode a polypeptide. The boundaries of the non-coding region are located before the start codon and after the stop codon. The non-coding region includes the untranslated regions of the genomic DNA.

"Endogenous gene" refers to the native gene normally found in its natural location in the genome.

"Transgene" refers to a gene that is introduced by gene transfer into the host organism.

"Coding sequence" refers to that portion of the gene that contains the information for encoding a polypeptide. The boundaries of the coding sequence are determined by a start codon at the 5' (amino) terminus and a translation stop codon at the 3' (carboxyl) terminus. A coding sequence can include, for example, prokaryotic sequences, cDNA from eukaryotic mRNA, genomic DNA, and even synthetic DNA sequences.

"Promoter" (or promoter sequence) refers to a DNA sequence, in a given gene, which sequence controls the expression of the coding sequence by providing the recognition site for RNA polymerase and other factors required for proper transcription. Most genes have regions of DNA sequence that are promoter sequences which regulate gene expression. Promoter regions are typically found in the 5' flanking DNA sequence upstream from the coding sequence in both prokaryotic and eukaryotic cells. A promoter sequence provides for regulation of transcription of the downstream gene sequence and typically includes from about 50 to about 2000 nucleotide base pairs. Promoter sequences also contain regulatory sequences such as enhancer sequences that can influence the level of gene expression. Some isolated promoter sequences can provide for gene expression of heterologous DNAs, that is DNA different from the natural homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. An isolated promoter sequence that is a strong promoter for heterologous DNAs is advantageous because it provides for a sufficient level of gene expression to allow for easy detection and selection of transformed cells, and provides for a high level of gene expression when desired. A promoter may also contain DNA sequences that are involved in the binding of protein factors which control the effectiveness of transcription initiation in response to physiological or developmental conditions.

"Regulatory sequence(s)" refers to nucleotide sequences located upstream (5'), within, and/or downstream (3') of a coding sequence, which control the transcription and/or expression of the coding sequences in conjunction with the protein biosynthetic apparatus of the cell. Regulatory sequences include promoters, translation leader sequences, transcription termination sequences and polyadenylation sequences.

"Encoding" and "coding" refer to the process by which a gene, through the mechanisms of transcription and translation, provides the information to a cell from which a series of amino acids can be assembled into a specific amino acid sequences to produce an active enzyme. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequences, such as deletions, insertions or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence to study the effect of retention of biological activity of the protein. Each of these proposed modifications is well within the routine skill in the art, as is the determination of retention of biological activity in the encoded products. Moreover, the skilled artisan recognizes that sequences encompassed by this invention are also defined by their ability to hybridize, under stringent condition, with the sequences exemplified herein.

"Expression" is meant to refer to the production of a protein product encoded by a gene. "Overexpression" refers to the production of a gene product in transgenic organisms that exceed levels of production in normal or non-transformed organisms.

"Functional portion" or "functional fragment" or "functional equivalent" of an enzyme is that portion, fragment, or equivalent which contains the active site for binding one or more reactants or is capable of improving or regulating the rate of reaction. The active site may be made up of separate portions present on one or more polypeptide chains and will generally exhibit high substrate specificity.

"Enzyme encoded by a nucleotide sequence" includes enzymes encoded by a nucleotide sequence which includes partial isolated DNA sequences.

"Transformation" refers to the transfer of a foreign gene into the genome of a host organism and its genetically stable inheritance.

"% identity" refers to the percentage of the nucleotides/amino acids of one polynucleotide/polypeptide that are identical to the nucleotides/amino acids of another sequence of polynucleotide/polypeptide as identified by a program such as GAP from Genetics Computer Group Wisconsin (GCG) package (version 9.0) (Madison, Wis.). GAP uses the algorithm of Needleman and Wunsch (J. Mol. Biol. 48: 443-453, 1970) to find the alignment of two complete sequences that maximizes the number of matches and minimizes the number of gaps. When parameters required to run the above algorithm are not specified, the default values offered by the program are contemplated.

"Substantial homology" or "substantial similarity" refers to a 70% or more similarity or 70% homology wherein "% similarity" or "% homology" between two polypeptide sequences is a function of the number of similar positions shared by two sequences on the basis of the scoring matrix used divided by the number of positions compared and then multiplied by 100. This comparison is made when two sequences are aligned (by introducing gaps if needed) to determine maximum homology. The PowerBlast program, implemented by the National Center for Biotechnology Information, can be used to compute optimal, gapped alignments. GAP program from Genetics Computer Group Wisconsin package (version 9.0) (Madison, Wis.) can also be used.

"Lignin monomer composition" refers to the relative ratios of guaiacyl monomer and syringyl monomer found in lignified plant tissue.

"Plant" includes whole plants and portions of plants, including plant organs (e.g., roots, stems, leaves, etc).

"Angiosperm" refers to plants that produce seeds encased in an ovary. A specific example of an angiosperm is *Liquidambar styraciflua* (L.)[sweetgum].

"Gymnosperm" refers to plants that produce naked seeds, i.e., seeds that are not encased in an ovary. A specific example of a gymnosperm is *Pinus taeda* (L.)[loblolly pine].

"Isolated" and/or "purified" in reference to a nucleic acid molecule or polypeptide are meant to refer to in vitro isolation of a nucleic acid or polypeptide molecule from its natural cellular environment, and from association with other components of the cell so that it can be sequenced, replicated and/or expressed.

"Vector" is a recombinant nucleic acid construct, such as a plasmid, phage, genome, virus genome, cosmid, or artificial chromosome, to which a polynucleotide of the present invention may be attached. In a specific embodiment, the vector may bring about the replication of the attached segment, e.g., in the case of a cloning vector.

"Sinapyl alcohol dehydrogenase" or "SAD" refers to the enzyme in the plant phenylpropanoid biosynthetic pathway, which catalyzes the conversion of sinapaldehyde to sinapyl alcohol and permits the production of syringyl lignin. In the illustrated embodiment of the present invention, the SAD DNA sequence (FIG. 2A) was identified from quaking aspen, *Populus tremuloides*. It is understood that this sequence can be used as a probe to clone its equivalent (i.e., with substantial homology or substantial identity is defined herein) from any plant species by techniques (EST, PCR, RT-PCR, anti-SAD antibodies, anti-SAD polypeptide antibodies, etc.) well known in the art. SAD DNA sequence is defined herein as any DNA sequences that encode enzymes capable of catalyzing specifically the conversion of sinapaldehyde into sinapyl alcohol according to the enzyme assay methods described herein. As one of skill in the art will appreciate, an amino acid sequence having less than 100% amino acid identity to SEQ ID NO:2 will retain SAD activity. It is specifically envisioned that a SAD coding sequence encoding a polypeptide having an amino acid identity of at least 95% identity and less than 99.8% identity to SEQ ID NO. 2 will be useful in the present invention.

The Phenyl Propanoid Biosynthetic Pathway:

Reference is made to FIG. 1 which shows different steps in the biosynthetic pathways from 4-coumarate (1) to guaiacyl (coniferyl alcohol (6)) and syringyl (sinapyl alcohol (9)) monolignols for the formation of guaiacyl-syringyl lignin together with the enzymes responsible for catalyzing each step. The enzymes indicated for each of the reaction steps are: 4-coumaric acid 3-hydroxylase (C3H) which converts 4-coumarate (1) to caffeate (2); 4-coumarate-CoA ligase (4CL) converts caffeate (2) to caffeoyl CoA (2) which in turn is converted to feruloyl CoA (4) by caffeoyl-CoA O-methyltransferase (CCoAOMT); cinnamoyl-CoA reductase (CCR) converts feruloyl CoA (4) to coniferaldehyde (5); coniferyl alcohol dehydrogenase (CAD) converts coniferaldehyde (5) to the guaiacyl monolignol coniferyl alcohol (6); at coniferaldehyde (5), the pathway splits wherein coniferaldehyde (5) can also be converted to 5-hydroxyconiferaldehyde (7) by coniferaldeyde 5-hydroxylase (CAld5H); 5-hydroxyconiferaldehyde O-methyltransferase (AldOMT) converts 5-hydroxconiferaldehyde (7) to sinapaldehyde (8) which, in turn, is converted to the syringyl monolignol, sinapyl alcohol (9) by sinapyl alcohol dehydrogenase (SAD).

It had been previously reported that this final step to the formation of sinapyl alcohol was catalyzed by CAD. The present invention is the first disclosure of a separate enzyme for the formation of sinapyl alcohol from sinapaldehyde. CAD and SAD together regulate the quantity and composition of guaiacyl-syringyl lignin. The present invention provides an isolated SAD protein and SAD cDNA clones, which can now be used to modify lignification. SEQ ID NO 1 gives the sequence listing for the SAD cDNA from *Populus tremuloides*, while SEQ ID NO 2 gives the sequence listing for the deduced SAD polypeptide.

A comparison of the amino acid sequences of all reported CAD-like enzymes to the novel SAD enzyme of the present invention is provided in Table 1 below. CAD has been characterized for several different species. The values listed in Table 1 indicate the percent amino acid identity. Table 1 illustrates that SAD exhibits only about 50% amino acid sequence identity to all other known CADs, demonstrating that SAD is a different and novel enzyme with different biochemical function from other CADs. Therefore, the SAD protein sequence is phylogenetically distinguishable from the sequences of all currently known monolignol CADs.

DNA Constructs

According to the present invention, there is provided a DNA construct which is a plant DNA having a promoter sequence, a coding region and a terminator sequence. The coding region encodes the SAD enzyme essential to lignin biosynthesis. The coding region is suitably a minimum size of 50 bases. The gene promoter is positioned at the 5'-end of a transgene (the transgene may be SAD alone or SAD together with another enzyme from the plant monolignols as described hereinafter) for controlling the transgene expression and a gene termination sequence that is located at the 3'-end of the transgene for signaling the end of the transcription of the transgene.

The DNA construct in accordance with the present invention is suitably incorporated into the genome of a plant by transformation to alter lignin biosynthesis, e.g., to provide syringyl-enriched lignin. The DNA construct may include clones provided herein, namely PtXAD (later renamed PtSAD), described hereinafter, and variants thereof such as are permitted by the degeneracy of the genetic code or the functional equivalents thereof.

The DNA constructs of the present invention may be inserted into plants to regulate production of the SAD enzyme. Depending on the nature of the construct, the production of the protein may be increased or reduced, either throughout or at particular stages in the life of the plant. For example, the orientation of the DNA coding sequence, promoter, and termination sequence can serve to either suppress lignin formation or amplify lignin formation. For the down-regulation of lignin synthesis, the DNA is in the antisense orientation. For the amplification of lignin biosynthesis, the DNA is in the sense orientation, thus to provide

TABLE 1

Comparison of all CAD-like protein sequences available in the database. Values indicate % amino acid sequence identity.

|    | 1  | 2  | 3  | 4  | 5  | 6  | 7  | 8  | 9  | 10 | 11 | 12 | 13 | 14 | 15 | 16 |
|----|----|----|----|----|----|----|----|----|----|----|----|----|----|----|----|----|
| 1  |    |    |    |    |    |    |    |    |    |    |    |    |    |    |    |    |
| 2  | 79 |    |    |    |    |    |    |    |    |    |    |    |    |    |    |    |
| 3  | 79 | 97 |    |    |    |    |    |    |    |    |    |    |    |    |    |    |
| 4  | 80 | 85 | 84 |    |    |    |    |    |    |    |    |    |    |    |    |    |
| 5  | 80 | 82 | 82 | 84 |    |    |    |    |    |    |    |    |    |    |    |    |
| 6  | 79 | 80 | 80 | 81 | 94 |    |    |    |    |    |    |    |    |    |    |    |
| 7  | 79 | 81 | 81 | 82 | 80 | 78 |    |    |    |    |    |    |    |    |    |    |
| 8  | 79 | 81 | 80 | 81 | 80 | 78 | 80 |    |    |    |    |    |    |    |    |    |
| 9  | 73 | 78 | 77 | 79 | 76 | 74 | 76 | 77 |    |    |    |    |    |    |    |    |
| 10 | 73 | 78 | 78 | 79 | 77 | 74 | 76 | 76 | 99 |    |    |    |    |    |    |    |
| 11 | 73 | 77 | 76 | 78 | 74 | 73 | 75 | 74 | 95 | 96 |    |    |    |    |    |    |
| 12 | 67 | 70 | 71 | 69 | 70 | 70 | 69 | 68 | 67 | 68 | 68 |    |    |    |    |    |
| 13 | 68 | 69 | 70 | 69 | 69 | 69 | 69 | 68 | 67 | 67 | 67 | 99 |    |    |    |    |
| 14 | 67 | 69 | 70 | 68 | 69 | 69 | 68 | 68 | 67 | 67 | 67 | 99 | 95 |    |    |    |
| 15 | 68 | 69 | 69 | 70 | 70 | 69 | 68 | 68 | 69 | 69 | 67 | 95 | 95 | 94 |    |    |
| 16 | 51 | 53 | 53 | 54 | 53 | 52 | 52 | 53 | 49 | 50 | 48 | 53 | 53 | 54 | 54 |    |

1: *M. sativa*, AF083332;
2: PtCAD, AF217957;
3: *P. deltoides*, z19568;
4: *A. corada*, D13991;
5: *N. tabacum*, x62343;
6: *N. tabacum*, x62344;
7: *E. globulus*, AF038561;
8: *E. gunnii*, x65631;
9: *Z. mays*, aj005702;
10: *Z. mays*, y13733;
11: *S. offininarum*, AJ231135;
12: *P. radiada*, u62394;
13: *P. taeda*, z37992;
14: *P. taeda*, z37991;
15: *P. abies*, x27675;
16: PtXAD (renamed PtSAD).

one or more additional copies of the DNA in the plant genome. In this case, the DNA is suitably a full-length cDNA copy. It is also possible to target expression of the gene to specific cell types of the plants, such as the epidermis, the xylem, the roots, etc. Constructs in accordance with the present invention may be used to transform cells of both monocotyledons and dicotyledons plants in various ways known in the art. In many cases, such plant cells may be cultured to regenerate whole plants which subsequently reproduce to give successive generations of genetically modified plants. Examples of plants that are suitably genetically modified in accordance with the present invention, include but are not limited to, trees such a aspen, poplar, pine and eucalyptus.

Promoters and Termination Sequences

Various gene promoter sequences are well known in the art and can be used in the DNA constructs of present invention. The promoter in a construct of the present invention can provide for expression of the linked DNA segment. The promoter can also be inducible so that gene expression can be turned on or off by an exogenously added agent. It may also be preferable to combine the desired DNA segment with a promoter that provides tissue specific expression or developmentally regulated gene expression in plants.

The promoter may be selected from promoters known to operate in plants, e.g., CaMV35S, GPAL2, GPAL3 and endogenous plant promoter controlling expression of the SAD enzyme, i.e., the endogenous promoter of the SAD gene. Use of a constitutive promoter such as the CaMV35S promoter (Odell et al. 1985), or CaMV 19S (Lawton et al., 1987) can be used to drive the expression of the transgenes in all tissue types in a target plant. Other promoters are nos (Ebert et al. 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated with the R gene complex (Chandler et al., 1989). On the other hand, use of a tissue specific promoter permits functions to be controlled more selectively. The use of a tissue-specific promoter has the advantage that the SAD enzyme is only produced in the tissue in which its action is required. Suitably, tissue-specific promoters, such as those that confine the expression of the transgenes in developing xylem where lignification occurs, may be used in the inventive DNA constructs.

A DNA segment can be combined with the promoter by standard methods as described in Sambrook et al., 2nd ed. (1982). Briefly, a plasmid containing a promoter such as the CaMV35S promoter can be constructed as described in Jefferson (1987) or obtained from Clontech Lab, Palo Alto, Calif. (e.g., pBI121 or pBI221). Typically, these plasmids are constructed to provide for multiple cloning sites having specificity for different restriction enzymes downstream from the promoter. The DNA segment can be subcloned downstream from the promoter using restriction enzymes to ensure that the DNA is inserted in proper orientation with respect to the promoter so that the DNA can be expressed.

The gene termination sequence is located 3' to the DNA sequence to be transcribed. Various gene termination sequences known in the art may be used in the present inventive constructs. These include nopaline synthase (NOS) gene termination sequence (see, e.g., references cited in co-pending, commonly-owned PCT Application "Method to Introduce Multiple Genes into Plants", Ser. No. PCT/US00/27704, filed Oct. 6, 2000).

Marker Genes

A marker gene may also be incorporated into the inventive DNA constructs to aid the selection of plant tissues with positive integration of the transgene. "Marker genes" are genes that impart a distinct phenotype to cells expressing the marker gene and thus, allow such transformed cells to be distinguished from cells that do not have the marker. Many examples of suitable marker genes are known to the art and can be employed in the practice of the invention, such as neomycin phosphotransferase II (NPT II) gene that confers resistance to kanamycin or hygromycin antibiotics which would kill the non-transformed plant tissues containing no NPT II gene (Bevan et al., 1983). Numerous other exemplary marker genes are described in co-pending, commonly owned PCT Application "Method to Introduce Multiple Genes into Plants", Ser. No. PCT/US00/27704, filed Oct. 6, 2000, incorporated herein by reference.

Transformation

Transformation of tissues or cells from plants, for instance, trees, with the inventive DNA construct and the subsequent production of transgenic plants can be achieved by a variety of techniques known in the art. For example, Agrobacterium- and microprojectile-mediated techniques for transferring a DNA construct into host plant tissues are particularly suitable for tree species (Tsai et al., 1994; Ellis et al. 1993; and others described in co-pending, commonly owned PCT Application, PCT/US00/27704, filed Oct. 6, 2000 "Method to introduce multiple genes into plants", incorporated herein by reference). After transformation, transgenic plant tissues resistant to, e.g., antibiotics, such as kanamycin, can be selected and cultured to regenerate whole plants, using techniques also well known in the art (Tsai et al., 1994; Ellis et al. 1993; and others described in co-pending, commonly owned PCT Application, PCT/US00/27704 (supra)).

Transformation and regeneration protocols are readily adaptable to many plant species. Many transformation and regeneration protocols have been published for plant species. (See, co-pending, commonly-owned PCT Application Ser. No. PCT/US00/27704 (supra)).

DNA Clones

Figure 5:
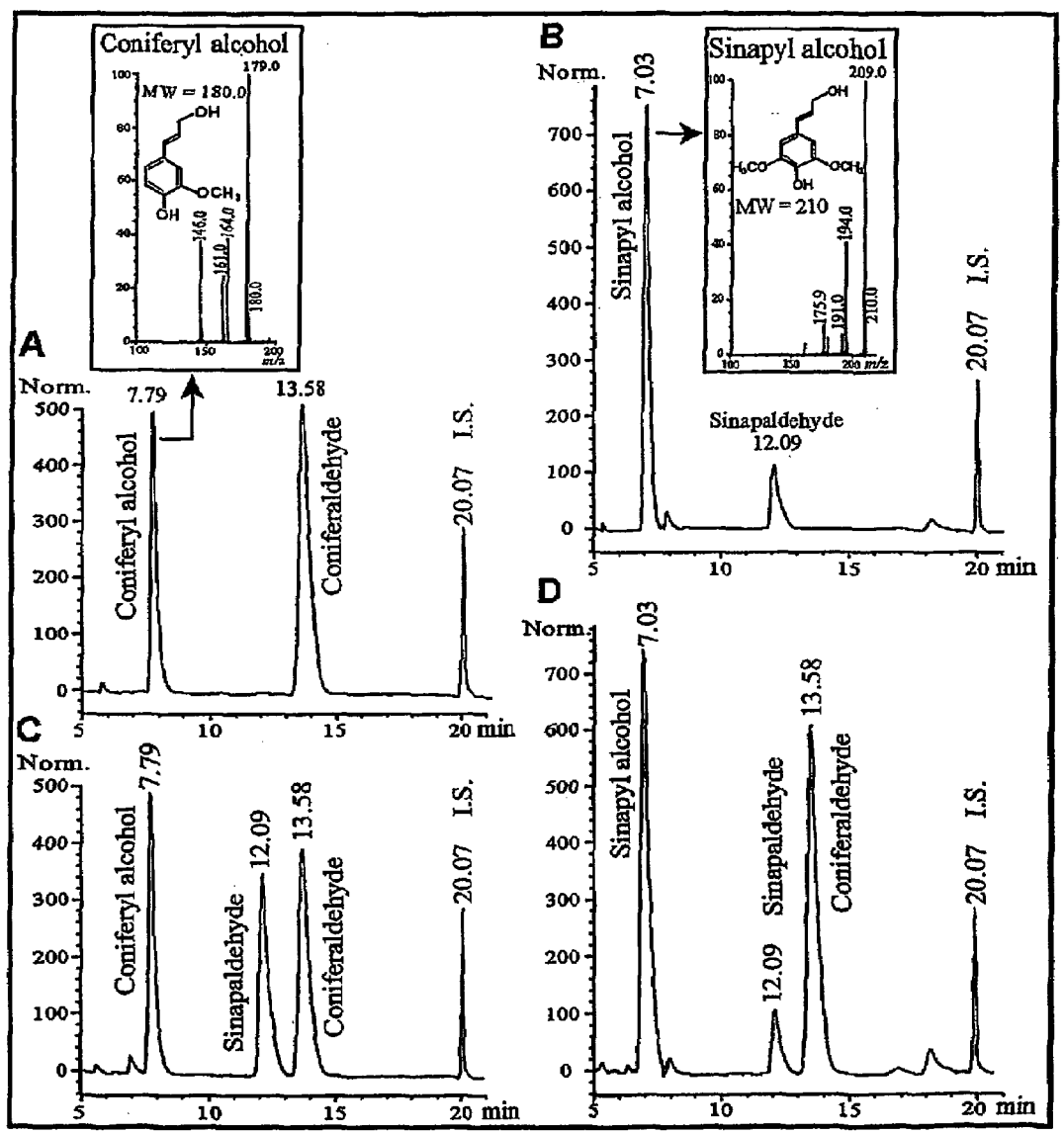
FIG. 5 illustrates HPLC-UV/MS analysis of recombinant PtCAD and PtSAD reactions.
Figure 6:
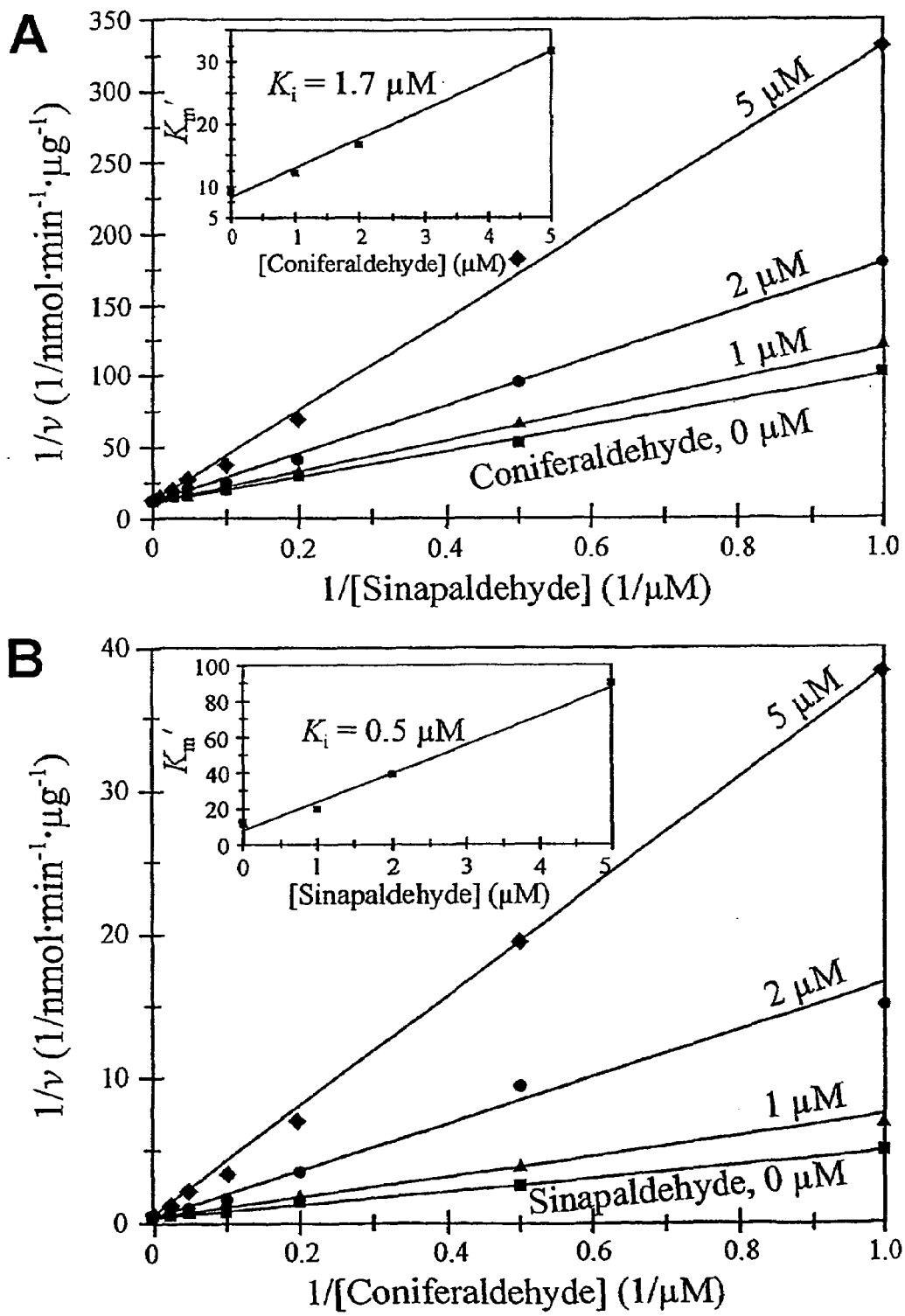
FIG. 6 illustrates inhibition kinetics of PtCAD and PtSAD.

A guaiacyl pathway gene encoding coniferyl alcohol dehydrogenase (CAD, FIG. 1) from *Populus tremuloides* (GenBank #AF217957) was first cloned. This cDNA was designated as PtCAD (GenBank #AF217957). *E. coli*-expressed recombinant PtCAD protein was characterized for its catalytic activity with coniferaldehyde and sinapaldehyde. Because monolignol biosynthetic pathway intermediates are present together in lignifying tissues (Osakabe et al., 1999; Li et al. 2000), the PtCAD enzyme activity with a mixture of coniferaldehyde and sinapaldehyde was assayed. As shown in FIG. 5(a) and (c), the reaction mixture was separated by HPLC after the enzyme reaction. Only coniferyl alcohol was formed from coniferaldehyde, as corroborated by mass spectrometry-based chemical structural analysis, and PtCAD had no reaction with sinapaldehyde. Thus, PtCAD has a specific catalytic reaction function with coniferaldehyde for the biosynthesis of guaiacyl monolignol, coniferyl alcohol (FIG. 1). CAD's substrate specificity for coniferaldehyde also confirms that there is a need for another enzyme, SAD of the present invention, in the biosynthesis of syringyl monolignol, sinapyl alcohol, as illustrated in FIG. 1.

A differential cloning strategy was designed to isolate candidate SAD genes based on their discernable sequences from that of CAD, as described above. Low- and high-stringency differential screening (further described in Example 2 herein below) of $1.8 \times 10^4$ pfu from the *Populus tremuloides* xylem cDNA library using PtCAD cDNA as a probe resulted in the isolation of two groups of positive clones, based on sequence analysis, i.e., Group I sequences and Group II sequences. Group I sequences of 12 clones were identical to PtCAD, and the sequences of group II cDNAs were identical to each other but different from PtCAD. Two of the 8 clones in group II were full-length cDNAs and designated as PtSAD. PtSAD cDNA (SEQ ID NO: 1) is 1,446-bp long, encoding an ORF of 362 amino acids (SEQ ID NO: 2) with a calculated MW of 38,991 and a pI of 6.69. Co-factor and zinc binding sequences identified in common alcohol dehydrogenases (ADHs) (Jornvall et al., 1987; O'Malley et al., 1992; Galliano et al., 1993) were found in PtSAD cDNA. Zn1 binding motif and the structural Zn2 consensus were located at amino acid residues 71 to 85 and residues 91 to 117, respectively. An NADP-binding site was identified at residues 191 to 196.

Figure 3:
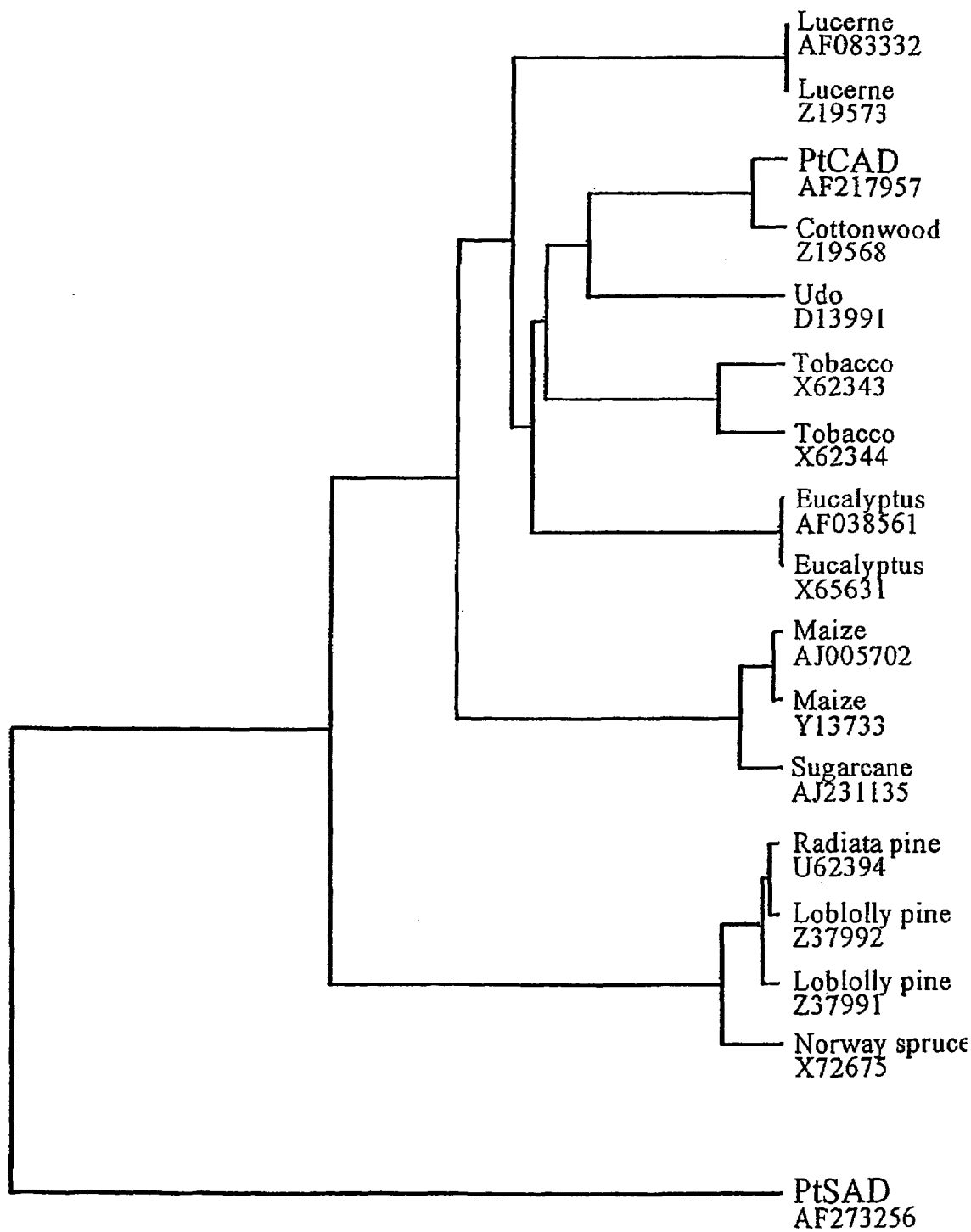
FIG. 3 is a phylogenetic analysis of Aspen SAD and plant CADs.

Furthermore, PtSAD exhibited only about 50% amino acid sequence identity to all the other known full-length monolignol CADs (see, Table 1 supra). However, it showed insignificantly low amino acid sequence identity (10-40%) to those ADHs considered to be associated with pathogen-defense functions (Jornvall et al., 1987; Brill et al., 1999). These sequence characteristics confirm that PtSAD belongs to a novel class of ADHs, discernable from the commonly known monolignol CADs. This is fully supported by the phylogenetic analysis of PtSAD and available full-length monolignol CAD protein sequences showing that these monolignol CADs (FIG. 3) form a cluster distinctly separated from PtSAD. This cluster of monolignol CADs is guaiacyl-specific in view of the extensive amino acid sequence similarity (~80 to 98%) of these genes with the guaiacyl-specific PtCAD and with CADs from loblolly pine and spruce, the single-copy gene involved in the biosynthesis of guaiacyl monolignol in gymnosperms (O'Malley et al., 1992; Galliano et al., 1993; MacKay et al. 1995). Thus, the phylogenetic analysis may reflect an ancient divergence of the guaiacyl CAD phylogenetic group into a more syringyl-specialized one, to which PtSAD belongs. Repeated screening of independent sets of pfu from *Populus tremuloides* xylem cDNA libraries with either PtCAD or PtSAD cDNA probes always resulted in the isolation of clones identical to either PtCAD or PtSAD, indicating the two predominant monolignol ADHs in lignifying xylem, CAD and SAD.

To demonstrate the biochemical function of PtSAD gene, PtSAD cDNA was expressed in *E. coli* to produce its recombinant protein. When coniferaldehyde alone was incubated with PtSAD recombinant protein, HPLC-MS analysis of the enzyme reaction production demonstrated that PtSAD had a specific activity of 786 nmol/min/mg protein with coniferaldehyde. However, PtSAD had a specific activity of 6964 nmol/min/mg protein with sinapaldehyde, indicating that the catalytic efficiency of PtSAD with sinapaldehyde is 9 times higher than with coniferaldehyde. Thus, PtSAD is specific for sinapaldehyde and SAD sinapyl alcohol dehydrogenase catalyzes the conversion of sinapaldehyde to sinapyl alcohol.

Proof of the sinapaldehyde-specific nature of PtSAD came from the PtSAD recombinant protein reaction with a mixture of coniferaldehyde and sinapaldehyde. HPLC-MS analysis (FIG. 5) of the reaction of PtSAD with a mixture of coniferaldehyde and sinapaldehyde demonstrated conclusively that sinapyl alcohol is the exclusive product from sinapaldehyde and that in an in vivo situation PtSAD would not react with coniferaldehyde.

Thus, taken together, CAD is guaiacyl-specific for the formation of guaiacyl monolignol, coniferyl alcohol, and SAD catalyzes the exclusive biosynthesis of syringyl monolignol, sinapyl alcohol. Furthermore, these results suggest discrete roles in plants for CAD and SAD proteins in coordinating cell-specific biosynthesis of guaiacyl and syringyl lignins.

A cDNA encoding this SAD enzyme has now been cloned for the first time. It was concluded that the presence of SAD enzyme is essential for the biosynthesis of syringyl lignin in plants, and that the incorporation of an SAD gene into transgenic plants is a viable mechanism for successful engineering of syringyl lignin in plants.

The invention will be further described by the following non-limiting examples.

EXAMPLE 1

Isolation of SAD cDNA from Aspen *Populus tremuloides*

An aspen developing xylem cDNA library was constructed in 8gt22A vector according to manufacturer's protocols (GIBCO BRL). The aspen CAD cDNA (GenBank #AF217957) was used as a probe to differentially screen the cDNA library under high and low stringency hybridization conditions. About 6,000 pfu from the cDNA library were lifted onto 4 individual nylon membranes. Two such blotted membranes were hybridized with $^{32}$P-labeled CAD cDNA probe under low stringency conditions (50° C.) and the other two under high stringency (65° C.). In this way, a total of 18,000 pfu were screened. High density hybridization signals were detected on membranes probed under either high or low stringency conditions. However, low density signal were detected only on membranes probed under low stringency condition. The high density signals on high stringency membrane were perfectly aligned with the high density signals on low stringency membrane, allowing a differential isolation of positive clones with low density signal. The high density clones were confirmed to be aspen CAD cDNA. The positives with low density signal were further screened until a single clone was isolated. The purified 8gt22A clones were then subcloned into pBluescriptS/K plasmid vector through NotI and EcoRI cloning sites. The sequencing results indicated that the isolated cDNA clone is 1,425-bp long (SEQ ID NO: 1) and encodes a 362 amino acid protein (SEQ ID NO: 2) which shows a 53% sequence identity with aspen CAD protein. This cDNA clone was first designated as PtXAD and then renamed as SAD after its biochemical function was confirmed.

Sequences of clones that hybridized with the probe only under low stringency conditions were identical to each other but distinct from PtCAD. Two of these low stringency probe-hybridizing clones were found to be full-length cDNAs; they were designated PtSAD and sequenced (ABI31O; Perkin-Elmer) in both directions (GenBank accession number AF273256).

EXAMPLE 2

Cloning of a Novel Alcohol Dehydrogenase Gene, PtSAD, from Aspen

To test the hypothesis of distinct CAD and SAD genes in angiosperms, CAD cDNA, PtCAD, was cloned from developing xylem of aspen and used to screen for related sequences in the same species. Low- and high-stringency differential screening of 2.4×10$^4$ plaque-forming units from an aspen xylem cDNA library (Wu et al., 2000) resulted in the isolation of two groups of positive clones. Group I contained 12 cDNAs with sequences identical to PtCAD. Sequences of the eight cDNAs constituting group II were identical to each other but differed from PtCAD. Two of the eight clones in group II were full-length cDNAs and were tentatively named PtSAD.

The open reading frame of PtSAD was 1086 bp, encoding a 39-kD protein with a pI of 6.69. The deduced amino acid sequence of PtSAD was 53% identical to that of PtCAD and ~50% identical to that of other angiosperm monolignol CADs, but it exhibited insignificant identity (10 to 40%) with the sequences of alcohol dehydrogenases (ADHs) associated with pathogen defense (Brill et al., 1999). PtCAD, on the other hand, showed extensive amino acid sequence identity with CADs from *Populus* trichocarpa X *Populus deltaides* (97%) (PtCADA; Van Doorsselaere et al., 1995), *Eucalyptus gunnii* (81%) (pEuCAD2; Grima-Pettenati et al., 1993), tobacco (82%) (pTCAD14; Knight et al., 1992), lucern (79%) (MsaCad2; Brill et al., 1999), and other reported angiosperms (~80%) (Brill et al., 1999). Therefore, PtSAD belongs to a novel class of ADHs.

Cofactor and zinc binding sequences conserved in ADHs (Jornvall et al., 1987) were present in PtSAD (FIG. 1). The Zn1 binding motif and structural Zn2 consensus regions (Jornvall et al., 1987; MacKay et al., 1995) were located at amino acid residues 71 to 85 and 91 to 117, respectively. A NADP binding site (Jornvall et al., 1987) was identified at residues 191 to 196. Repeated screening of the aspen xylem cDNA library with either PtCAD or PtSAD cDNA probes always resulted in the isolation of clones identical to either PtCAD or PtSAD, indicating that they are the two predominant monolignol-related ADHs in lignifying xylem.

Phylogenetic analysis of PtSAD and available full-length monolignol CAD protein sequences showed that gymnosperm and angiosperm CADs form a cluster that does not include PtSAD (FIG. 2). The angiosperm monolignol CADs in this cluster share ~70% amino acid sequence identity with gymnosperm CADs but ~50% with PtSAD, suggesting that all of these putative angiosperm monolignol CADs may be guaiacyl specific. These results also may reflect a divergence of the guaiacyl CAD phylogenetic group into a more syringyl-specialized group, to which PtSAD belongs.

EXAMPLE 3

DNA and RNA Gel Blot Analysis

Aspen genomic DNA and total RNA from various aspen tissues were isolated as described (Li et al., 1997; Hu et al., 1998). To determine whether there are other PtCAD and PtSAD related sequences in aspen, a gel blot analysis was done with aspen genomic DNA digested by various restriction enzymes and hybridized with either PtCAD (FIG. 4A) or PtSAD (FIG. 4B) full-length cDNA probes. DNA and RNA gel blot hybridizations were performed under high stringency conditions (Hu et al., 1998). Probes were PtCAD or PtSAD cDNA labeled with $\alpha$-$^{32}$P-dATP (Amersham) using the DECA prime labeling system (Ambion, Austin, Tex.).

There was a strong single band in each lane, but a weak single band also was detected in each lane, perhaps evidence of a distantly related sequence. Together with our cDNA screening results, we interpret these data to indicate that PtCAD and PtSAD likely are the predominant members of a small gene family in aspen.

DNA gel blot analysis also clearly demonstrated that PtCAD and PtSAD did not cross-hybridize with each other.

Figure 4:
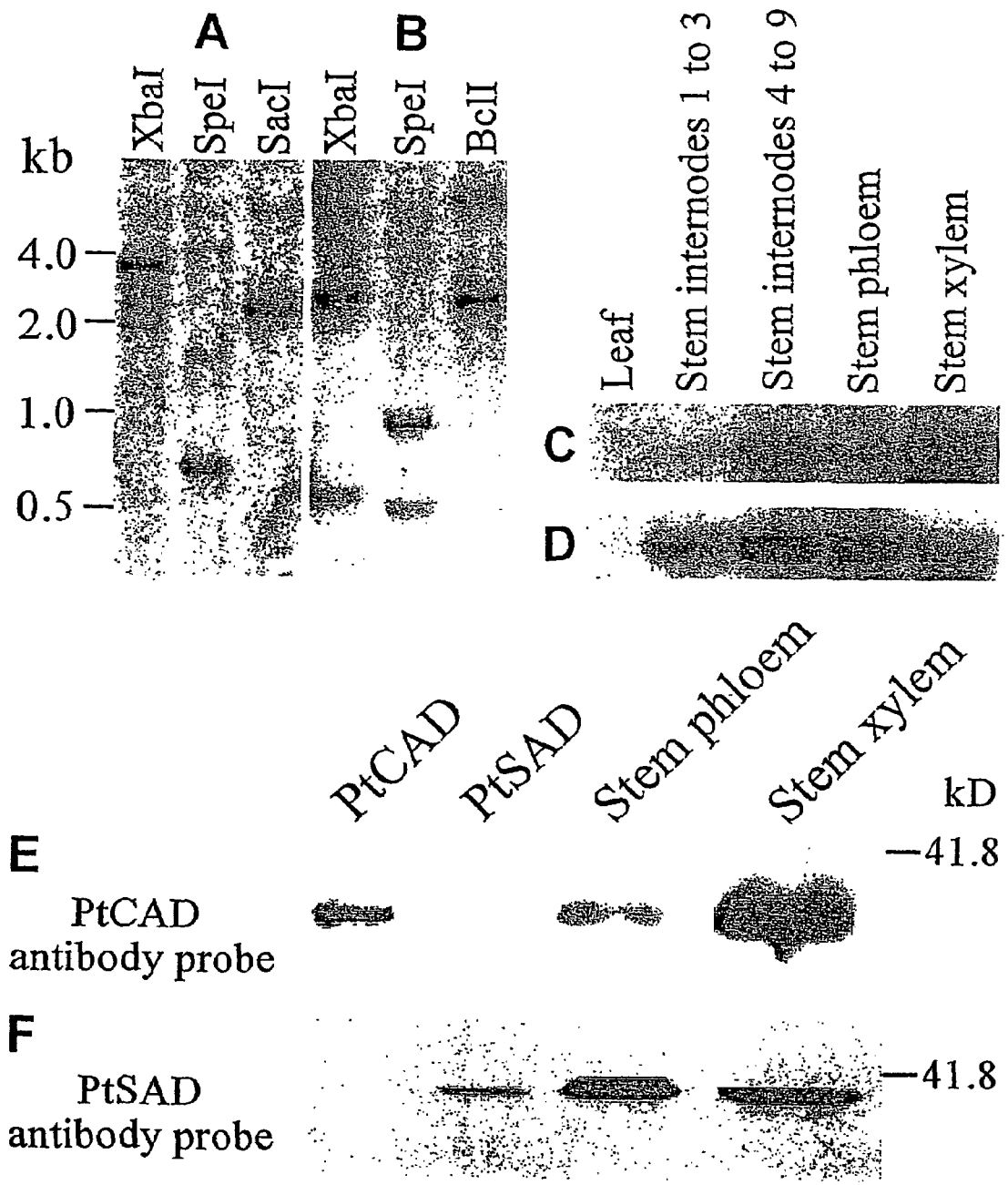
FIG. 4 illustrates molecular characterization of Aspen PtCAD and PtSAD.

Thus, using the same hybridization conditions and PtCAD and PtSAD full-length cDNA probes, RNA gel blot analysis was conducted to investigate the tissue-specific expression of PtCAD and PtSAD in aspen. The greatest PtCAD expression was found in tissue types containing a large amount of lignifying xylem, but its expression was lower in phloem-enriched tissues (internodes 1 to 3; FIG. 4C). Strong expression of PtSAD was detected in tissues undergoing rapid phloem (internodes 1 to 3; FIG. 4D) and xylem (internodes 4 to 9; FIG. 4D) development. The expression of PtCAD and PtSAD was not observed in leaves in which vascular midveins were removed.

Protein gel blot analysis was also conducted to verify the tissue-specific expression of PtCAD and PtSAD. Polyclonal antisera was obtained against affinity-purified PtCAD and PtSAD recombinant proteins produced in *Eschenchia coli* and protein gel blotting was used to verify the specificity of PtCAD and PtSAD antibodies against PtCAD and PtSAD recombinant proteins. For the various recombinant protein amounts (up to 75 ng) tested, PtCAD antibody did not cross-react with PtSAD protein (FIG. 4E), and PtSAD antibody did not cross-react with PtCAD protein (FIG. 4F). The PtCAD protein exhibited the expected molecular mass of ~39 kD and was more abundant in protein extracts from xylem than from phloem tissue (FIG. 4E). In contrast, the strongest signal using PtSAD antibody was detected in phloem protein extracts (FIG. 4F). RNA and protein gel blot analyses consistently indicated that both PtCAD and PtSAD were associated with lignification. Strong PtSAD expression in syringyl lignin-enriched phloem (Grand et al., 1982) suggests a specialized role for PtSAD in syringyl monolignol biosynthesis. Therefore, characterized herein are the biochemical functions of the PtCAD and PtSAD genes.

EXAMPLE 4

Determination of Enzyme Activity

To determine the enzyme activity of Aspen SAD having the amino acid SEQ ID NO: 2, the following experiments were conducted:

(i) Expression and Purification of PtCAD and PtSAD Recombinant Proteins and Preparation of Plant Protein Extracts The coding sequences of PtCAD and PtSAD were amplified by polymerase chain reaction (PCR) using primers designed to introduce Nde1 and Not1 sites immediately upstream of their start and stop codons, a sense primer SEQ ID NO: 3 (5'GG<u>CATATG</u>TCCAAGTCACCAGAA3') and an antisense primer SEQ ID NO: 4 (5'T<u>GCGGCCGC</u>GGGCTTCGTAGCTGCCAA3'). The PCR product was cloned into the Nde1 and Not1 sites of pET23$^{b+}$ vector (Novagen, Madison, Wis.) to fuse a His tag at the Carboxyl terminus of the cloned sequence. After sequence confirmation, the engineered pET23$^{b+}$ construct was transferred into *Escherichia coli* host strain BL21(DE3) (Novagen). Induction and purification of recombinant PtCAD and PtSAD were performed as described (Li et al., 2000). Differentiating stem xylem was collected during the growing season from aspen, hophorn beam (*Ostrya virginiana*), yellow birch (*Betula alleghaniensis*), sugar maple (*Acer saccharum*), red maple (*Acer rubrum*), sweetgum (*Liquidambar styraciflua*), and loblolly pine (*Pinus taeda*) and used to isolate crude protein extracts as described (Li et al., 2000).

(ii) Preparation of Anti-PtCAD and Anti-PtSAD Antibodies and Protein Gel Blot Analysis The affinity-purified PtCAD and PtSAD recombinant proteins were used to immunize rabbits (Alpha Diagnostic, San Antonio, Tex.). The antibodies, diluted 1:3000, were used in protein gel blot analyses of xylem crude proteins (Osakabe et al., 1999). Protein concentrations were determined by the Bio-Rad protein assay system.

(iii) SAD Enzyme Activity Assay

The SAD enzyme reactions were conducted in a final volume of 300 μl containing 100 mM sodium phosphate buffer, 500 μM substrate syringyl aldehyde (or coniferyl aldehyde), 1 μg recombinant SAD protein, 2.5 mM β-mercaptoethanol and 500 μM NADPH, with varying pHs (5.4, 6.0, 6.4, 7.0, 7.4, 8.0 or 8.4). After 10 min at 30° C., the reaction was terminated and extracted with 0.5 ml ethyl acetate. The extraction was repeated 4 times and the combined ethyl acetate was evaporated and dissolved in the HPLC mobile phase for LC-MS identification and quantitation of the reaction products as we did before (Osakabe et al., 1999; Li et al. 2000). An optimal pH of 7.0 was found for SAD reactions. The SAD reactions with mixed substrates, sinapaldehyde and coniferyl aldehyde, were therefore conducted at the optimal pH 7.0 under above-described conditions.

(iv) HPLC-UV/MS Analysis of Enzyme Functions and Reaction Kinetics

The basic enzyme reaction mixture contained 50 mM sodium phosphate buffer, 5 mM β-mercaptoethanol, 500 μM NADPH or NADP, purified recombinant protein (boiled protein was used as a control), and phenolic substrate in a final volume of 500 μL For the substrate specificity test, 500 μM aldehyde substrate and 1 μg of purified recombinant PtCAD or PtSAD protein (~25 pmol) were used. To characterize the enzyme pH optima, the substrate and recombinant PtCAD or PtSAD protein concentrations described above were used in sodium phosphate buffers, pH 5 to 8.5. All reactions were for 10 minutes at 30° C.

For normal and inhibition kinetic analyses, the reaction time was 4 min and pH was 8.0 for PtCAD (1.2 μg of purified recombinant protein) and 7.0 for PtSAD (0.1 μg). For kinetics, varying concentrations (0.5 to 200 μM) of p-coumaraldehyde, caffealdehyde, coniferaldehyde, 5-hydroxyconiferaldehyde, or sinapaldehyde were used to measure $K_m$, $V_{max}$, and the enzyme turnover number, $k_{cat}$. For inhibition kinetics, the PtCAD-mediated reduction of sinapaldehyde (1 to 200 μM) was assayed in the presence of 1 to 5 μM coniferaldehyde, and the PtSAD-catalyzed reduction of coniferaldehyde (1 to 200 μM) was assayed in the presence of 1 to 5 μM sinapaldehyde. All reactions were terminated by the addition of 10 μL of 6 N HCl (to bring the pH to 2) and 500 ng of internal standard o-coumaric acid and analyzed by HPLC-UV/MS.

An aliquot of 100 μL of reaction mixture was injected directly onto a Supelcosil LC-ABZ column (15 cm×4.6 mm×5 μm; Supelco, Bellefonte, Pa.) with automatic sample injection and separated isocratically with a Hewlett-Packard (HP) 1100 liquid chromatography system at 40° C. and a flow rate of 0.25 mL/min. The gradient program was 20% acetonitrile in 10 mM formic acid, pH 2.5, for 12 min, 20 to 100% acetonitrile from 12 to 16 min, and hold at 100% acetonitrile for 5 to 10 min; detection was with an HP 1100 diode array detector and an HP 1100 liquid chromatography-MS detector system with an atmospheric pressure onization-electrospray source in negative ion mode. The reaction products were identified and confirmed by comparing the ion fragmentation patterns of the product and the authentic standard in MS scanning mode at 70 V. The product quantity and $K_m$, $V_{max}$, $k_{cat}$, and apparent inhibition constant ($K_i$) values (means±SE) were determined as described (Osakabe et al., 1999; Li et al., 2000). The results of the inhibition kinetics for both the CAD enzyme (i.e. Table 2) and the SAD enzyme (i.e., Table 3) using a variety of substrates are illustrated below.

TABLE 2

Kinetic Properties of the Recombinant PtCAD Protein

| Substrate | $K_m$ (μM) | $V_{max}$ (nmol min$^{-1}$ μg$^{-1}$) | $k_{cat}$[a] (min$^{-1}$) | $V_{max}/K_m$ (%) |
|---|---|---|---|---|
| p-Coumaraldehyde | 6.2 ± 1.1 | 0.17 ± 0.04 | 6.8 ± 0.2 | 30.1 |
| Caffealdehyde | 37.0 ± 5.4 | 0.15 ± 0.03 | 6.0 ± 0.2 | 4.4 |
| Coniferaldehyde | 2.3 ± 0.8 | 0.21 ± 0.03 | 8.4 ± 0.3 | 100 |
| 5-Hydroxyconiferaldehyde | 17.5 ± 2.5 | 0.17 ± 0.04 | 6.8 ± 0.4 | 10.6 |
| Sinapaldehyde | 9.1 ± 1.2 | 0.10 ± 0.01 | 4.0 ± | 12.0 |

[a]$k_{cat}$, enzyme turnover number
Values are means ± SE for three independent assays.

TABLE 3

Kinetic Properties of the Recombinant PtSAD Protein

| Substrate | $K_m$ (μM) | $V_{max}$ (nmol min$^{-1}$ μg$^{-1}$) | $k_{cat}$[a] (min$^{-1}$) | $V_{max}/K_m$ (%) |
|---|---|---|---|---|
| p-Coumaraldehyde | 15.6 ± 1.4 | 2.9 ± 0.3 | 116 ± 11 | 27.4 |
| Caffealdehyde | 140.0 ± 9.1 | 2.0 ± 0.1 | 80 ± 4 | 2.2 |
| Coniferaldehyde | 12.7 ± 1.5 | 2.3 ± 0.2 | 92 ± 6 | 26.6 |
| 5-Hydroxyconiferaldehyde | 36.1 ± 2.3 | 3.8 ± 0.4 | 152 ± 16 | 15.5 |
| Sinapaldehyde | 7.4 ± 1.1 | 5.0 ± 0.3 | 200 ± 13 | 100 |

[a]$k_{cat}$, enzyme turnover number
Values are means ± SE for three independent assays.

EXAMPLE 5

Chemical Synthesis and Thioacidolysis Analysis of Aspen Stem Monolignol Composition All aldehydes and their alcohol derivatives were obtained from Sigma/Aldrich, except the following: p-coumaraldehyde, p-coumaryl alcohol, caffealdehyde, caffeyl alcohol, 5-hydroxyconiferaldehyde, and 5-hydroxyconiferyl alcohol were prepared chemically from their corresponding benzaldehyde derivatives as described (Osakabe et al., 1999; Li et al., 2000). The structural identities of these compounds were confirmed by $^1$H-NMR p-Coumaraldehyde: δ (acetone-$d_6$; standard carbon numbers were used) 6.48(1H, dd, J1=15.9, J2=7.8, $C_8$H), 6.80 (2H, m, Ar—H), 7.46 (1H, d, J=15.8, $C_7$H), 7.48 (2H, m, Ar—H), 9.50 (1H, d, $C_9$H); p-coumaryl alcohol: δ (acetone-$d_6$) 4.18 (2H, dd, J1=4, J2=1, $C_9$H), 6.19 (1H, dt, J1=15.9, J2=5.5, $C_8$H). 6.49 (1H, d, J=15.9, $C_7$M), 6.78 (2H, m, Ar—H), 7.26 (2M, m, Ar—H); caffealdehyde: δ (acetone-$d_6$) 6.53 (1H, dd, J1=15.7, J2=7.6, $C_8$H), 6.90 (1H, d, J=7.9, $C_5$H), 7.10 (1H, dd, J1=7.9, J2=2.1, $C_6$H), 7.20(1H, d, J2.1, $C_2$H), 7.51 (1H, d, J=15.7, $C_7$H), 9.61 (1H, d, J=7.6, $C_9$H); caffeyl alcohol: δ (acetone-$d_6$) 4.17 (2H, d, J5.5, $C_9$H), 6.14 (1H, dt, J1=15.9, J2=5.5, $C_8$H), 6.43 (1H, dt, J1=15.9, J2=1.5, $C_7$H), 6.75 (2H, d, J=1.5, $C_5$H, $C_6$H), 6.92 (1H), d, J=1.5, $C_2$H); 5-hydroxyconiferaldehyde: δ (acetone-$d_6$) 3.88 (3H, s, $OCH_3$), 6.60. (1H, dd, J1=15.6, J2=7.8, $C_8$H), 6.88 (1H, d, J=1.7, $C_6$H), 6.95 (1H, d, J=1.7, $C_2$H), 7.50 (1H, d, J=15.6, $C_7$H), 9.61 (1H, d, J=7.8, $C_9$H); 5-hydroxyconiferyl alcohol: δ (acetone-$d_6$) 3.87 (3H, s, $OCH_3$), 4.28 (2H, t, J=5.5, $C_9$H), 6.20 (1H, dt, J1=15.9, J2=5.5, $C_8$H), 6.47 (1H, d, J=15.9, $C_7$H), 6.51 (1H, d, J=1.8, $C_6$H), 6.64 (1H, d.J=1.8, $C_2$H). For analysis of monolignol composition, aspen stem internodes were extracted with benzene/alcohol and subjected to gas chromatography-mass spectrometry (MS)-based thioacidolysis (Rolando et al., 1992; Tsai et al., 1998).

EXAMPLE 6

Histochemical Lignin Analysis, Immunolocalizatlon, and Microscopy

For histochemical localization of lignin, fresh hand-cut sections (~20 μm thick) from stem internodes of 4-month-old, greenhouse-grown aspen plants (clone 271) were incubated immediately in freshly prepared saturated chlorinated water for 10 min at 4° C. After three washes with water, the sections were incubated in 4% sodium sulfite at room temperature for 5 min, mounted in 50% glycerol, and photographed using a Nikon (Tokyo, Japan) Eclipse 400 fluorescence microscope. Segments (~1 mm thick) from the same internodes used for histochemical analysis were used for immunolocalization on the basis of the protocol of Wittich et al. (1999) with modifications. The segments were fixed in 4% paraformaldehyde in 0.1 M PBS (4 mM sodium phosphate, pH 7.4, and 200 mM NaCl) for 12 hr at 4° C. After washing in PBS for 2 hr at 4° C., the segments were dehydrated in an ethanol series, infiltrated, and embedded in butyl methyl methacrylate.

Polymerization was performed under UV light (365 nm) for 40 hr at −20° C. in a UVC2 CRYO Chamber (PELCO, Redding, Calif.). Sections (3 μm thick) were prepared with a Leica (wetzlar, Germany) RM 2155 microtome and mounted on Superfrost/plus (Fisher) slides. Slides were rinsed with acetone to remove butyl methyl methacrylate from the sections, which were rehydrated in an ethanol series and blocked first with 0.1 M hydroxyammonium chloride for 5 min and then with 1% BSA for 30 min at room temperature. After incubation with anti-PtCAD, anti-PtCAld5H (Osakabe et al., 1999), anti-PtAldOMT (Li et al., 2000), or anti-PtSAD antibodies (in 1:500 dilution) for 2 hr at 37° C., slides were washed in PBS containing 0.1% BSA and incubated with goat anti-rabbit antibody conjugated with alkaline phosphatase (1:100; Boehringer Mannheim) for 1.5 hr at 37° C. After washing in PBS, slides incubated with anti-PtSAD, antiPtCAld5H, or anti-PtAldOMT antibodies were reacted at pH 9.5 with a mixture of dimethylformamide and nitroblue tetrazolium/5-bromo-4-chloro-3-indolyl phosphate, and those incubated with anti-PtCAD antibodies were treated with Fast Red TR/Naphthol AS-MX (Sigma); both treatments were for 20 to 30 min at room temperature. Pre-immune serum was used as the control. The slides then were mounted in 50% glycerol and observed with a Nikon Eclipse 400 microscope, and images were taken using a Sony (Tokyo, Japan) DKC-5000 digital photo camera.

EXAMPLE 7

Histochemical and Chemical Detection of Guaiacyl and Syringyl Lignin Distributions in Aspen Stem Vascular Tissues The in situ relationship between PtCAD/PtSAD and guaiacyl syringyl lignin biosynthesis was identified by analyzing the distribution of guaiacyl and syringyl lignins in vascular systems of the aspen stem. Syringyl lignin can be distinguished chromogenically from guaiacyl lignin in situ by Cross/Bevan or Maule color reaction (Nakano and Meshitsuka, 1992). The lignin-based chromophore-forming mechanisms in these two methods are similar. The chlorination of the syringyl nucleus leads to a pink (lignifying cells) or red (lignified cells) color, whereas the guaiacyl nucleus produces a light (lignifying cells) to dark (lignified cells) brown color (Bland, 1966; Wardrop, 1981). The Cross/Bevan method was used in these experiments because of its mild reaction conditions, circumventing the problem of thin tissue section destruction that often occurs during Maule color reactions.

Figure 7:
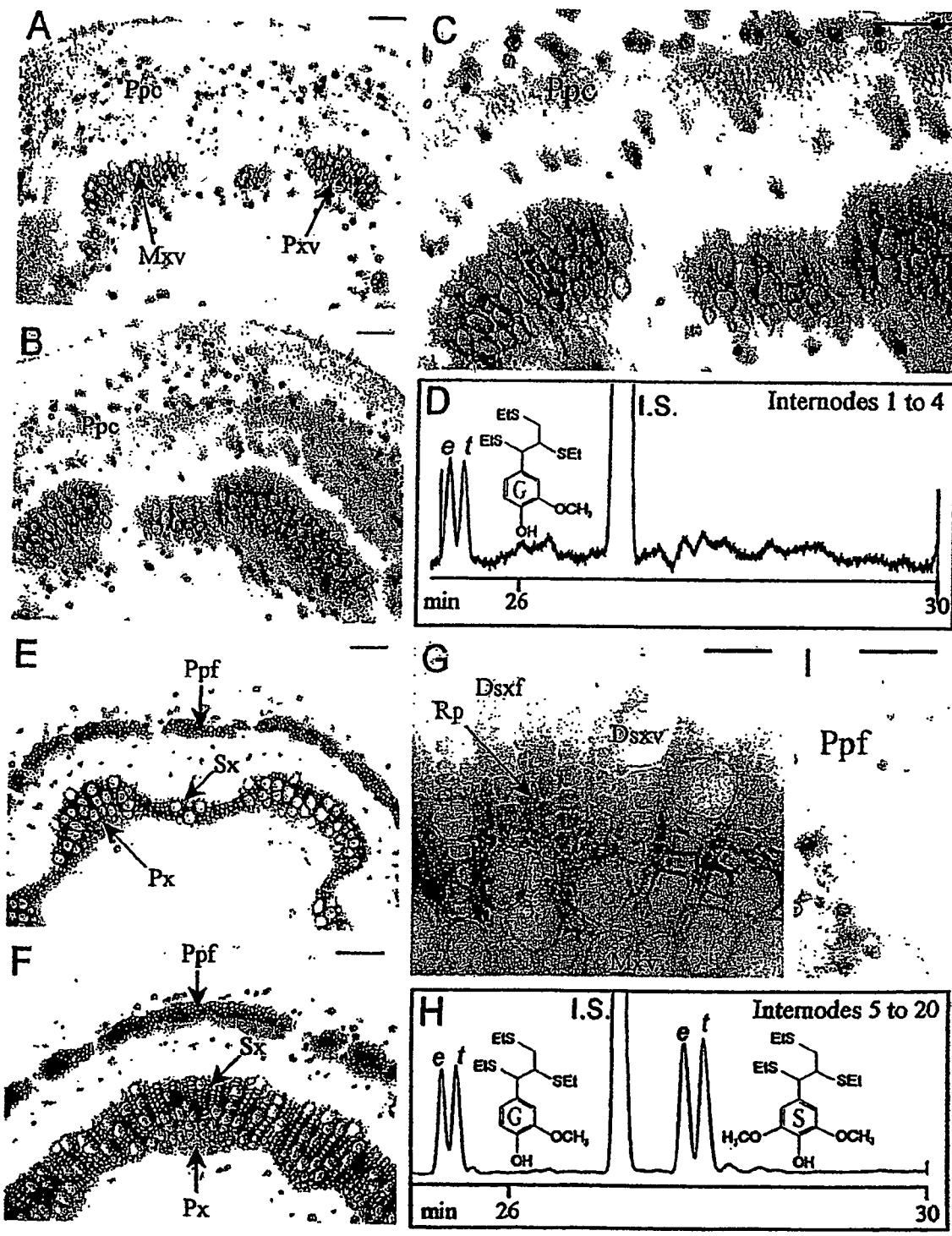
FIG. 7 illustrates the location of guaiacyl and syringyl lignins in Aspen stem.

In the primary vascular tissues, lignin was observed only in xylem and was of the guaiacyl type, as revealed by the brown staining of protoxylem and metaxylem vessel elements between stem internodes 1 and 4 (FIGS. 7A and 7B). This was further confirmed by thioacidolysis analysis of stem lignin, which demonstrated the exclusive detection of guaiacyl monomers (FIG. 7D). The primary xylem remained as the only stem tissue containing pure guaiacyl lignin (FIGS. 7E to 7G). Guaiacyl-syringyl lignin appeared during the differentiation of secondary vascular systems, as indicated by the chemical analyses of stem internodes 5 and beyond (FIG. 7H). However, the deposition of syringyl lignin in the secondary xylem followed that of guaiacyl lignin, as manifested by the color change from bright light brown to pink and then red in developing, partially lignified, and extensively lignified secondary xylem elements, respectively (FIG. 7G). This is consistent with the reported sequential deposition of guaiacyl followed by syringyl lignins in xylem cells of angiosperms (Terashima et al., 1986; Saka and Goring, 1988).

Aggregated protophloem parenchyma cells, the precursors of primary phloem fibers (Esau, 1965), were present in primary growth tissues (FIGS. 7A to 7C), but these cells were not stained for lignin, likely because of their lack of secondary wall thickening. They also failed to stain for guaiacyl lignin once lignification and secondary thickening began (FIG. 7I). Instead, syringyl-positive pink (FIG. 7I) to red (FIGS. 7E and 7F) coloration prevailed in these cells as they differentiated into fibers. Indeed, phloem fibers are known for their enrichment in syringyl lignin, but they do accumulate guaiacyl-syringyl lignin (Grand et al., 1982). Together, these observations indicate that in direct contrast to the lignification sequence in secondary xylem elements, the biosynthesis of syringyl lignin precedes and overwhelms that of guaicyl lignin in primary phloem fibers.

Immunolocalization was used to verify whether PtCAD is associated with guaiacyl lignin-synthesizing primary xylem and whether the distribution of PtCAD and PtSAD is in line with the guaiacyl and syringyl lignin deposition patterns in phloem and xylem elements. The distribution of another syringyl pathway protein, PtCAd5H, also was analyzed.

EXAMPLE 8

Immunolocalization of PtCAD, PtCAd5H, and PtSAD in Aspen Stem Internodes

Figure 8:
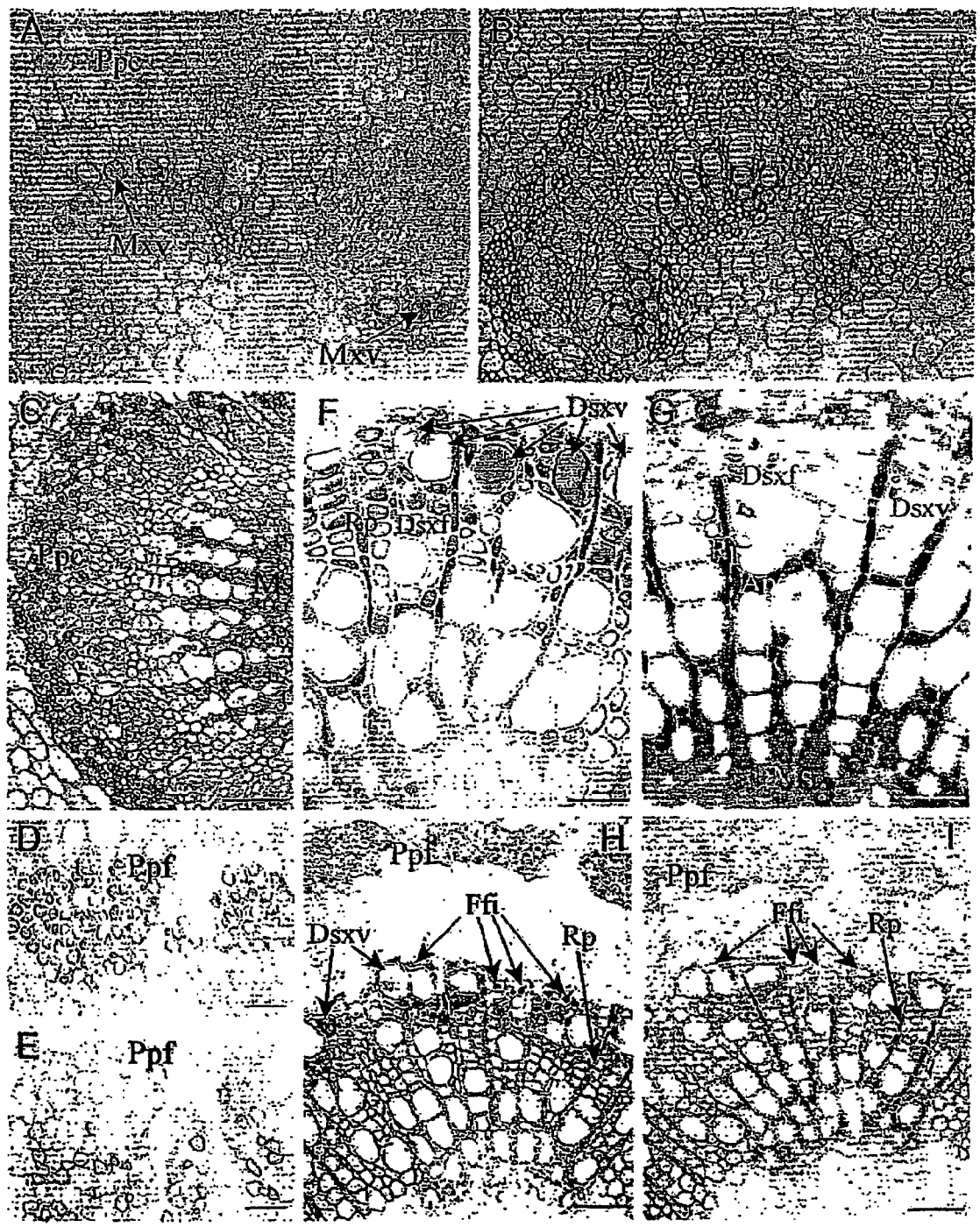
FIG. 8 illustrates the immunolocalization of PtCAld5H, and PtSAD proteins in Aspen stem.
Figure 9:
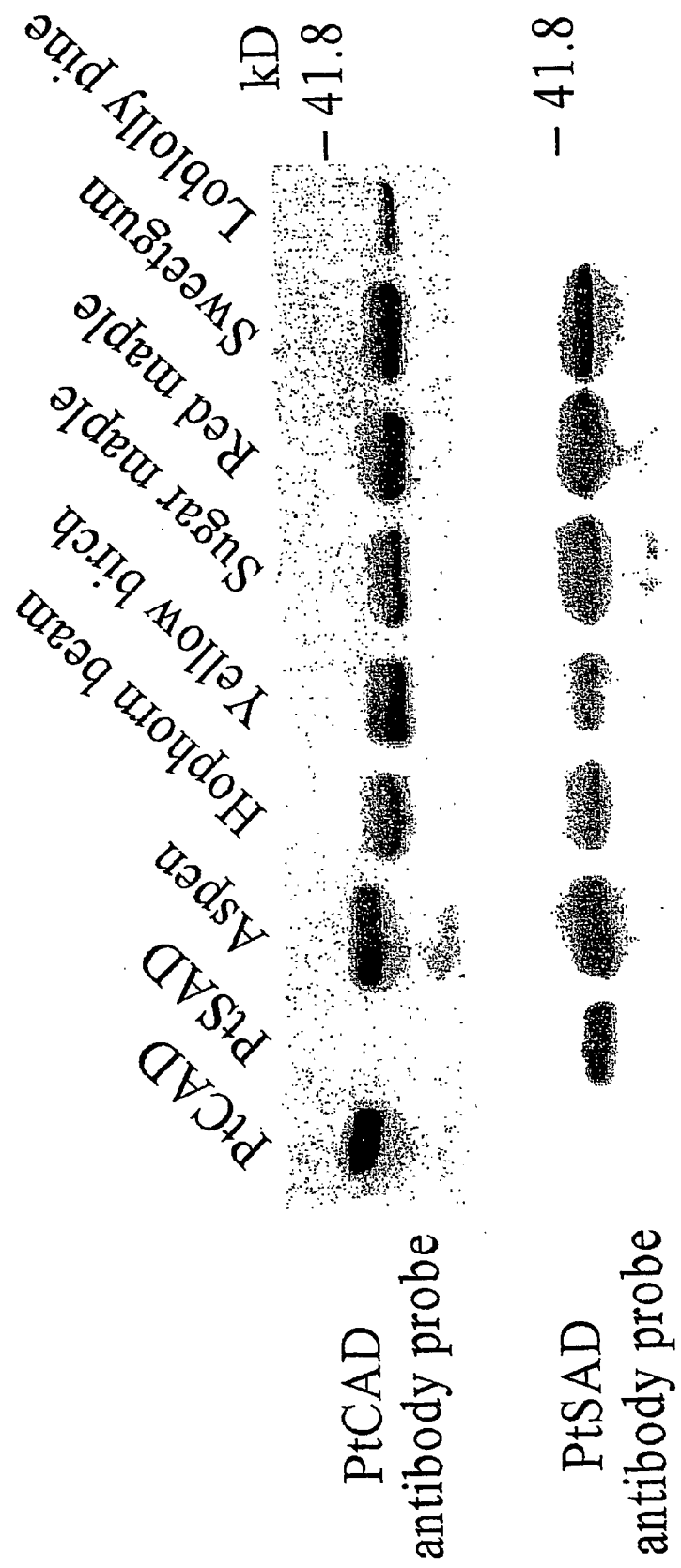
FIG. 9 illustrates the immuno-reactivity of CAD and SAD proteins in various plants.

Conditions similar to those present during protein gel blot analyses, by which the specificities of PtCAD and PtSAD antibodies were verified (FIGS. 4E and 4F), were applied to cellular immunolocalization. PtSAD and PtCAld5H were visualized in tissue sections after the anti-rabbit IgG-alkaline phosphatase reaction with nitroblue tetrazolium/5-bromo-4-chloro-3-indolyl phosphate substrate. PtCAD signals were visualized with Fast Red substrate. Serial sections were analyzed. Pre-immune serum used at the same protein concentration as the anti-PtCAD, anti-PtSAD, or anti-PtCAld5H antiserum gave no immunolabeling signal (data not shown). At the third internode, PtCAD was detected almost exclusively in developing metaxylem vessels (FIG. 8A). PtSAD was not detected in metaxylem vessels but was most conspicuous in protophloem parenchyma cells and in the parenchymatous storage tissue, the medullary sheath (FIG. 8B).

The cellular distribution of PtCAld5H (FIG. 8C) conformed with that of PtSAD. At the third internode, the lignification and secondary wall thickening had begun in metaxylem vessels but not in protophloem parenchyma cells (FIGS. 7A to 7C). Consistently, no lignin color reaction was observed in protophloem parenchyma cells (FIG. 7A), despite the detection in these cells of PtSAD and PtCAld5H (FIGS. 8B and 8C). However, at internode 6, both syringyl lignin deposition (FIG. 7I) and PtSAD signals (data not shown) were observed in these cells undergoing differentiation into primary phloem fibers. At the eighth internode, PtSAD signals diminished in these differentiating fiber cells (FIG. 8E), signifying the near completion of syringyl monolignol biosynthesis in these cells (FIG. 7E).

At this stage, PtCAD became more conspicuous than PtSAD in these maturing fibers (FIG. 8D), indicative of an active biosynthesis of guaiacyl monolignol. As the primary phloem continued its centripetal course of differentiation, new protophloem parenchyma cells appeared adjacent to the maturing fibers toward the center of the stem. These new primary phloem fiber precursors (Esau, 1965) were labeled with PtSAD (FIG. 8E) but not yet with PtCAD (FIG. 8D). At internode 12, PtSAD signals disappeared in primary phloem fibers (FIG. 8I), suggesting the completion of syringyl monolignol biosynthesis in these cells. However, PtCAD signals remained strong in these maturing fibers (FIG. 8H). At internode 15, neither PtCAD nor PtSAD was detected in these fibers that became fully lignified (data not shown). These results agree with those of histochemical lignin localization indicating that the biosynthesis of syringyl lignin precedes that of guaiacyl lignin in primary phloem fibers.

However, these procambium-derived primary phloem elements and the secondary xylem exhibited contrasting lignification sequences. PtCAD appeared in xylem fusiform initials before PtSAD (FIGS. 8H and 8I), consistent with chemical and histochemical evidence that the biosynthesis of syringyl lignin lags behind that of guaiacyl lignin in the secondary xylem. Furthermore, in the differentiating secondary xylem, PtCAD signals were most conspicuous in maturing vessels (FIGS. 8F and 8H) but also were strong in developing fiber and ray cells. PtSAD signals were strongest in syringyl lignin-enriched radial and axial ray cells (FIG. 8G) (Wardrop and Dadswell, 1952; Musha and Goring, 1975) and were conspicuous in maturing fiber cells but were nearly absent from developing vessels (FIGS. 8G and 8I). These protein distribution patterns in the secondary xylem were sustained through older internodes (data not shown). These results and histochemical observations consistently demonstrated that PtCAD is associated with cells specializing in guaiacyl lignin synthesis and that PtSAD and PtCAd5H are associated with vascular elements containing enriched syringyl lignin.

EXAMPLE 9

Production of Syringyl-Enriched Lignin in Transformed Plants

The following genetic transformations illustrate production of syringyl-enriched lignin in plants.

A. To produce syringyl-enriched lignin in angiosperm plants, angiosperm plants are genetically transformed with sense SAD gene driven by any appropriate promoter and via any appropriate genetic transformation system.

B. To produce syringyl-enriched lignin in gymnosperm plants, gymnosperm plants are genetically transformed with sense SAD genes driven by any appropriate promoter and via any appropriate genetic transformation system.

The invention has now been described and exemplified with some specificity, those skilled in the art will appreciate the various modifications, including variation, additions and omissions, that may be made in what has been described. Accordingly, it is intended that these modifications also be encompassed by the present invention and that the scope of the present invention be limited solely by the broadest interpretation that lawfully can be accorded the appended claims.

REFERENCES

Bevan et al., 1983, *Nature*, 304:184
Bugos et al., 1991, *Plant Mol. Biol.* 17:203.
Chang, H. M., and Sarkanen, K. V., 1973, *Tappi* 56:132.
Chiang, V. L., and Funaoka, M., 1990, *Holzforschung* 44:309.
Ellis et al., 1993, *Bio/Technology* 11:84.
Freudenberg, K., 1965, *Science* 148:595.
Baucher, et al., 1996, *Plant Physiol.* 112:1479.
Bland, D. E., 1966, *Holzforschung* 20:12.
Boudet, et al., 1995, *New Phytol.* 129:203.
Brill, et al., 1999, Plant Mol. Biol. 41:279.
Chen, et al., 1999, *Planta* 207: 597.

Corner, E. J. H., 1968, *The Life of Plants*. (New York: New American Library).
Esau, K., 1965, *Plant Anatomy*, 2nd ed. (New York: John Wiley and Sons).
Fergus, B. J., and Goring, D. A. I., 1970a, *Holzforschung* 24:113.
Fergus, B. J., and Goring, D. A. I., 1970b, *Holzforschung* 24:118.
Frey-Wyssling, A., and Bosshard, H. H., 1959, *Holzforschung* 13:129.
Galliano, et al., 1993a, *Plant Mol. Biol.* 23:145.
Galliano, et al., 1993b, *Phytochemistry* 32:557.
Goffner et al., 1992, *Planta* 188:48.
Goffner et al., 1994, *Plant Physiol.* 106:625.
Goffner et al., 1998, *Plant Mol. Biol.* 36:755.
Grand et al., 1982, *Holzforschung* 36:217.
Grima-Pettenati et al., 1993, *Plant Mol. Biol.* 21:1085.
Grima-Pettenati et al., 1994, *Phytochemistry* 37:941.
Gross, G. G., 1980, *Adv. Bot. Res.* 8:25.
Guo et al., 2001, *Plant Cell* 13:73.
Hahlbrock, K., and Scheel, D., 1989, *Plant Mol. Biol.* 40:347.
Halpin et al., 1992, *Plant Physiol.* 98:12.
Halpin et al., 1994, *Plant J.* 6:339.
Hawkins, S. E., and Boudet, A. M., 1994, *Plant Physiol.* 104:75.
Hibino et al., 1993a, *Phytochemistry* 32:565.
Hibino et al., 1993b, *Plant Cell Physiol.* 34:659.
Higuchi, T., 1997,. (New York: Springer-Verlag).
Higuchi et al., 1994, *J. Biotechnol.* 37:151.
Hu et al., 1998, *Proc. Natl. Acad. Sci. USA* 95:5407.
Hu et al., 1999, *Nat. Biotechnol.* 17:808.
Humphreys et al., 1999, *Proc. Natl. Acad. Sci. USA* 96:10045.
Jornvall et al., 1987, *Eur. J. Biochem.* 167:195.
Kawamura, I., and Higuchi, T., 1962, *J. Jpn. Wood Res. Soc.* 8:148.
Knight et al., 1992, *Plant Mol. Biol.* 19:793.
Kutsuki et al., 1982,. *Phytochemistry* 21:19.
Lacombe et al., 1997, *Plant J.* 11:429.
Li et al., 1997, *Proc. Nati. Acad. Sci. USA* 94:5431.
Li et al., 1999, *Plant Mol. Biol.* 40:555.
Li et al., 2000, *J. Biol. Chem.* 275:6537.
Lüderitz, T., and Grisebach, H., 1981, *Eur. J. Biochem.* 119:115.
MacKay et al., 1995, *Mol. Gen. Genet.* 247:537.
Mansell et al., 1974, *Phytochemistry* 13:2427.
Mansell et al., 1976, *Phytochemistry* 15:1849.
Musha, Y., and Goring, D. A. I., 1975, *Wood Sci. Technol.* 9:45.
Nakano, J., and Meshitsuka, G., 1992, C. W. Dence and SY. Lin, eds (New York: Springer-Verlag), 23.
O'Malley et al., *Plant Physiol.* 98:1364.
Osakabe et al., 1999, *Proc. Nati. Acad. Sci. USA* 96:8955.
Parvathi et al., 2001, *Plant J* 25:193.
Raven, J. A. (1977), *Advances in Botanical Research*, H. W. Woolhouse, ed (London: Academic Press), 153.
Rolando et al., 1992, *Methods in Lignin Chemistry*, C. W. Dence and S. Y. Lin, eds (New York: Springer-Verlag), 334.
Ryser, U., and Keller, B., 1992, *Plant Cell* 4:773.
Saka, S., and Goring, D. A. I., 1985, *Biosynthesis and Biodegradation of Wood Components*, T. Higuchi, ed (New York: Academic Press), 141.
Saka, S., and Goring, D. A. I., 1988, *Holzforschung* 42:149.
Samaj et al., 1998, *Planta* 204:437.
Sarkanen, K. V., and Hergert, H. L., 1971, *Lignins. Occurrence, Formation, Structure and Reaction*, K. V. Sarkanen and C. H. Ludwig, eds (New York: Wiley-Interscience), 43.
Sarni et al., 1984, *Eur. J. Biochem.* 139:259.
Sato et al., 1997, *Plant Physiol.* 113:425.
Scurfield, G., 1973, *Science* 179:647.
Scurfield, G., and Bland, D. E., 1963, *J Hortic. Sci.* 38:297.
Somssich et al., 1989, *Plant Mol. Biol.* 12:227.
Somssich et al., 1996, *Proc. Natl. Acad. Sci. USA* 93:14199.
Stewart et al., 1997, *Planta* 201:311.
Terashima et al., 1986, *Holzforschung* 42:101.
Towers, G. H. N., and Gibbs, R. D., 1953, *Nature* 172:25.
Trotter, P. C., 1990, *Tech. Assoc. Pulp Paper Ind. J.* 73:198.
Tsai et al., 1998, *Plant Physiol.* 117:101.
Umezawa, T., 1994, *Wood Molecular Biology*, T. Higuchi, ed (Tokyo: Buneido Publishing), 140.
Van Doorsselaere et al., 1995, *Plant Physiol. Biochem.* 33:105.
Wardrop, A. B., 1971, *Lignins: Occurrence, Formation, Structure and Reaction*, K. V. Sarkanen and C. H. Ludwig, eds (New York: Wiley-Interscience), 19.
Wardrop, A. B., 1981, *Xylem Cell Development*, J. R. Barnett, ed (Tunbridge Wells, UK: Castle House Publications), 115.
Wardrop, A. B., and Dadswell, H. E., 1952, *Aust. J Sci. Res. Ser. B Biol. Sci.* 5:223.
Wardrop, A. B., and Davies, G. W., 1964, *Aust. J Bot.* 12:24.
Wengenmayer et al., 1976, *Eur. J. Biochem.* 65:529.
Whetten, R., and Sederoff, R., 1995, *Plant Cell* 7:1001.
Whetten et al., 1998, *Annu. Rev. Plant Physiol. Plant Mol. Biol.* 49:585.
Wittich et al., 1999, *Protoplasma* 208:224.
Wu et al., 2000, *Plant J* 22:495.
Wyrambik, D., and Grisebach, H., 1975, *Eur. J. Biochem.* 59:9.
Wyrambik, D., and Grisebach, H., 1979, *Eur. J. Biochem.* 97:503.
Ye et al., 1994, *Plant Cell* 6:1427.
Zhang, X.-H., and Chiang, V. L., 1997, *Plant Physiol.* 113:65.
Zhong et al., 1998, *Plant Cell* 10:2033.
Zinser et al., 1998, *Planta* 204:169.

The invention claimed is:

1. An isolated polynucleotide encoding a polypeptide comprising an amino acid sequence having at least 95% and less than 99.8% amino acid sequence identity to SEQ ID NO: 2, wherein the polypeptide catalyzes the conversion of sinapaldehyde to sinapyl alcohol.

2. The polynucleotide of claim 1, wherein the polypeptide exhibits greater substrate specificity for sinapaldehyde than for coniferaldehyde.

3. The polynucleotide of claim 1, wherein the polypeptide has a lower $k_m$ for sinapaldehyde than for coniferaldehyde.

4. A DNA construct comprising the polynucleotide sequence of claim 1 operably linked to a promoter.

5. A plant cell comprising the construct of claim 4.

6. A plant comprising the cell of claim 5.

7. The plant of claim 6, wherein the plant exhibits increased expression of a polypeptide comprising a sequence having at least 95% and less than 99.8% amino acid sequence identity to SEQ ID NO: 2 and having the ability to catalyze the conversion of sinapaldehyde to sinapyl alcohol, relative to a control plant lacking the construct.

8. The plant of claim 6, wherein the plant exhibits increased expression of a polypeptide comprising a sequence having at least 95% and less than 99.8% amino acid sequence identity to SEQ ID NO: 2, relative to a control plant lacking the construct.

9. The plant of claim 6, wherein the plant is a tree.

10. The plant of claim 9, wherein the tree is selected from the group consisting of aspen, poplar, pine, and eucalyptus.

11. The plant of claim 9, wherein the tree is an angiosperm.

12. The plant of claim 9, wherein the tree is a gymnosperm.

13. The DNA construct of claim 4, wherein the promoter is selected from the group consisting of a constitutive promoter and a tissue-specific promoter.

14. The DNA construct of claim 13, wherein the promoter is xylem tissue-specific.

15. A method of increasing expression of sinapyl alcohol dehydrogenase in a plant cell comprising incorporating the construct of claim 4 into the genome of the plant cell.

* * * * *

SEQUENCE LISTING

```
<160> NUMBER OF SEQ ID NOS: 4

<210> SEQ ID NO 1
<211> LENGTH: 1446
<212> TYPE: DNA
<213> ORGANISM: aspen populus tremuloides
```

<400> SEQUENCE: 1

```
tttttttttt ttcctagcc ttccttctcg acgatatttc tctatctgaa gcaagcacca      60
tgtccaagtc accagaagaa gaacaccctg tgaaggcctt cgggtgggct gctagggatc    120
aatctggtca tctttctccc ttcaacttct ccaggagggc aactggtgaa gaggatgtga    180
ggttcaaggt gctgtactgc gggatatgcc attctgacct tcacagtatc aagaatgact    240
ggggcttctc catgtaccct ttggttcctg gcatgaaat tgtgggggaa gtgacagaag    300
ttgggagcaa ggtgaaaaag gttaatgtgg gagacaaagt gggcgtggga tgcttggttg    360
gtgcatgtca ctcctgtgag agttgtgcca atgatcttga aaattactgt ccaaaaatga    420
tcctgacata cgcctccatc taccatgacg gaaccatcac ttacggtggc tactcagatc    480
acatggtcgc taacgaacgc tacatcattc gattccccga taacatgccg cttgacggtg    540
gcgctcctct cctttgtgcc gggattacag tgtatagtcc cttgaaatat tttggactag    600
atgaacccgg taagcatatc ggtatcgttg gcttaggtgg acttggtcac gtggctgtca    660
aatttgccaa ggcctttgga tctaaagtga cagtaattag tacctcccct tccaagaagg    720
aggaggcttt gaagaacttc ggtgcagact cattttttggt tagtcgtgac caagagcaaa    780
tgcaggctgc cgcaggaaca ttagatggca tcatcgatac agtttctgca gttcaccccc    840
ttttgccatt gtttggactg ttgaagtctc acgggaagct tatcttggtg ggtgcaccgg    900
aaaagcctct tgagctacct gccttttctt tgattgctgg aaggaagata gttgccggga    960
gtggtattgg aggcatgaag gagacacaag agatgattga ttttgcagca aaacacaaca   1020
tcacagcaga tatcgaagtt atttcaacgg actatcttaa tacggcgata gaacgtttgg   1080
ctaaaaacga tgtcagatac cgattcgtca ttgacgttgg caatactttg gcagctacga   1140
agccctaagg agaagatccc atgttctcga accctttata aaatctgata acatgtgttg   1200
atttcatgaa taaatagatt atctttggga tttttcttta ataaacgaag tgttctcgaa   1260
aacttaacat cggcaatacc ctggcagcta cgagaaacgc tttagaattg tttgtaagtt   1320
tgtttcatta gggtgatacc atgctctcga gtcctttgta agatccattt atagttgcgt   1380
gaatgctatg aacaaataat atgtttgcgg cttctcttca aaaaaaaaaa aaaaaaaaa    1440
aaaaaa                                                                1446
```

<210> SEQ ID NO 2
<211> LENGTH: 362
<212> TYPE: PRT
<213> ORGANISM: aspen populus tremuloides

<400> SEQUENCE: 2

```
Met Ser Lys Ser Pro Glu Glu Glu His Pro Val Lys Ala Phe Gly Trp
1               5                   10                  15

Ala Ala Arg Asp Gln Ser Gly His Leu Ser Pro Phe Asn Phe Ser Arg
            20                  25                  30

Arg Ala Thr Gly Glu Glu Asp Val Arg Phe Lys Val Leu Tyr Cys Gly
        35                  40                  45

Ile Cys His Ser Asp Leu His Ser Ile Lys Asn Asp Trp Gly Phe Ser
    50                  55                  60

Met Tyr Pro Leu Val Pro Gly His Glu Ile Val Gly Glu Val Thr Glu
65                  70                  75                  80

Val Gly Ser Lys Val Lys Lys Val Asn Val Gly Asp Lys Val Gly Val
                85                  90                  95
```

```
Gly Cys Leu Val Gly Ala Cys His Ser Cys Glu Ser Cys Ala Asn Asp
            100                 105                 110

Leu Glu Asn Tyr Cys Pro Lys Met Ile Leu Thr Tyr Ala Ser Ile Tyr
            115                 120                 125

His Asp Gly Thr Ile Thr Tyr Gly Tyr Ser Asp His Met Val Ala
            130                 135                 140

Asn Glu Arg Tyr Ile Ile Arg Phe Pro Asp Asn Met Pro Leu Asp Gly
145                 150                 155                 160

Gly Ala Pro Leu Leu Cys Ala Gly Ile Thr Val Tyr Ser Pro Leu Lys
                165                 170                 175

Tyr Phe Gly Leu Asp Glu Pro Gly Lys His Ile Gly Ile Val Gly Leu
                180                 185                 190

Gly Gly Leu Gly His Val Ala Val Lys Phe Ala Lys Ala Phe Gly Ser
                195                 200                 205

Lys Val Thr Val Ile Ser Thr Ser Pro Ser Lys Lys Glu Glu Ala Leu
                210                 215                 220

Lys Asn Phe Gly Ala Asp Ser Phe Leu Val Ser Arg Asp Gln Glu Gln
225                 230                 235                 240

Met Gln Ala Ala Ala Gly Thr Leu Asp Gly Ile Ile Asp Thr Val Ser
                245                 250                 255

Ala Val His Pro Leu Leu Pro Leu Phe Gly Leu Leu Lys Ser His Gly
                260                 265                 270

Lys Leu Ile Leu Val Gly Ala Pro Glu Lys Pro Leu Glu Leu Pro Ala
                275                 280                 285

Phe Ser Leu Ile Ala Gly Arg Lys Ile Val Ala Gly Ser Gly Ile Gly
                290                 295                 300

Gly Met Lys Glu Thr Gln Glu Met Ile Asp Phe Ala Ala Lys His Asn
305                 310                 315                 320

Ile Thr Ala Asp Ile Glu Val Ile Ser Thr Asp Tyr Leu Asn Thr Ala
                325                 330                 335

Ile Glu Arg Leu Ala Lys Asn Asp Val Arg Tyr Arg Phe Val Ile Asp
                340                 345                 350

Val Gly Asn Thr Leu Ala Ala Thr Lys Pro
                355                 360

<210> SEQ ID NO 3
<211> LENGTH: 23
<212> TYPE: DNA
<213> ORGANISM: aspen populus tremuloides

<400> SEQUENCE: 3
ggcatatgtc caagtcacca gaa                                    23

<210> SEQ ID NO 4
<211> LENGTH: 27
<212> TYPE: DNA
<213> ORGANISM: aspen populus tremuloides

<400> SEQUENCE: 4
tgcggccgcg ggcttcgtag ctgccaa                                27
```